(12) United States Patent
Phillips

(10) Patent No.: US 9,398,771 B2
(45) Date of Patent: Jul. 26, 2016

(54) SPRAY APPARATUSES, USES OF DIATOMACEOUS EARTH, AND METHODS OF CONTROLLING INSECT POPULATIONS

(71) Applicant: Roderick William Phillips, Vancouver (CA)

(72) Inventor: Roderick William Phillips, Vancouver (CA)

(*) Notice: Subject to any disclaimer, the term of this patent is extended or adjusted under 35 U.S.C. 154(b) by 196 days.

(21) Appl. No.: 14/222,335

(22) Filed: Mar. 21, 2014

(65) Prior Publication Data

US 2014/0242136 A1  Aug. 28, 2014

Related U.S. Application Data

(63) Continuation of application No. PCT/CA2012/001015, filed on Nov. 1, 2012.

(60) Provisional application No. 61/563,220, filed on Nov. 23, 2011.

(30) Foreign Application Priority Data

Apr. 26, 2012 (WO) ................ PCT/CA2012/000389

(51) Int. Cl.
| | |
|---|---|
| *A01N 25/00* | (2006.01) |
| *A01N 65/03* | (2009.01) |
| *A01N 59/00* | (2006.01) |
| *C09K 3/30* | (2006.01) |
| *B65D 83/14* | (2006.01) |
| *B65D 83/20* | (2006.01) |

(52) U.S. Cl.
CPC ................ *A01N 65/03* (2013.01); *A01N 59/00* (2013.01); *B65D 83/752* (2013.01); *C09K 3/30* (2013.01); *B65D 83/20* (2013.01)

(58) Field of Classification Search
None
See application file for complete search history.

(56) References Cited

U.S. PATENT DOCUMENTS

| | | | |
|---|---|---|---|
| 1,569,710 | A | 1/1926 | Burt |
| 2,508,506 | A | 5/1950 | Fridolph |
| 2,687,537 | A | 8/1954 | Wallace et al. |

(Continued)

FOREIGN PATENT DOCUMENTS

| | | |
|---|---|---|
| CA | 1112158 | 11/1981 |
| CA | 2149164 A1 | 11/1996 |

(Continued)

OTHER PUBLICATIONS

Lebeau et al. Diatom cultivation and biotechnolgically relevant products, Part II Current and Putative Products, Appl Microbial Biotechnology, 2003 60:624-632.*

(Continued)

*Primary Examiner* — Anand Desai
*Assistant Examiner* — Melissa Mercier
(74) *Attorney, Agent, or Firm* — Kilpatrick Townsend & Stockton LLP

(57) ABSTRACT

There is disclosed a spray apparatus for holding contents comprising diatomaceous earth and a compressed propellant for propelling the diatomaceous earth. There is also disclosed use of diatomaceous earth to control a population of bedbugs, wherein the diatomaceous earth comprises remains of pennate diatoms. There is also disclosed a method of controlling a population of insects, the method comprising causing a compressed propellant to propel diatomaceous earth on a surface. Method of manufacturing a spray apparatus and methods of preparing diatomaceous earth for use in controlling a population of insects are also disclosed.

30 Claims, 20 Drawing Sheets

(56) References Cited

U.S. PATENT DOCUMENTS

| | | | |
|---|---|---|---|
| 3,010,615 | A | 11/1961 | Smith et al. |
| 3,082,147 | A | 3/1963 | Newallis et al. |
| 3,082,148 | A | 3/1963 | Baker et al. |
| 3,132,769 | A | 5/1964 | Zehrbach |
| 3,165,441 | A | 1/1965 | Ludvik et al. |
| 3,306,499 | A | 2/1967 | Lykes |
| 3,652,425 | A | 3/1972 | Wilson |
| 3,878,147 | A | 4/1975 | Craven |
| 4,008,688 | A | 2/1977 | Nicholas |
| 4,083,977 | A | 4/1978 | Miesel |
| 4,098,435 | A | 7/1978 | Weyn |
| 4,279,895 | A | 7/1981 | Carle |
| 4,526,305 | A | 7/1985 | Lykes |
| D286,378 | S | 10/1986 | Banfield |
| 4,821,349 | A | 4/1989 | Cohen |
| 5,074,348 | A | 12/1991 | Phillips |
| 5,176,435 | A | 1/1993 | Pipkens |
| 5,186,935 | A | 2/1993 | Tucker |
| 5,195,195 | A | 3/1993 | Murray |
| 5,269,032 | A | 12/1993 | Flocks |
| 5,308,613 | A | 5/1994 | Banfield |
| 5,346,296 | A | 9/1994 | Kelley |
| 5,773,017 | A | 6/1998 | Korunic et al. |
| 5,809,708 | A | 9/1998 | Greer et al. |
| 6,182,307 | B1 | 2/2001 | Rutrick |
| 6,196,156 | B1 | 3/2001 | Denesuk et al. |
| 6,276,102 | B1 | 8/2001 | Shipman et al. |
| 6,371,190 | B1 | 4/2002 | Owens |
| 6,375,969 | B1 | 4/2002 | Kostka et al. |
| 6,394,321 | B1 | 5/2002 | Bayer |
| 6,405,491 | B1 | 6/2002 | Gallant |
| 6,416,775 | B1 | 7/2002 | Kostka et al. |
| 6,506,409 | B1 | 1/2003 | Hoy et al. |
| 6,530,181 | B1 | 3/2003 | Seiber et al. |
| 6,543,071 | B1 | 4/2003 | Lenner |
| 6,581,807 | B1 | 6/2003 | Mekata |
| 6,618,876 | B2 | 9/2003 | Murphy et al. |
| 6,658,677 | B2 | 12/2003 | Paul |
| 7,118,179 | B1 | 10/2006 | Wilson et al. |
| 7,159,253 | B2 | 1/2007 | Yang |
| 7,387,151 | B1 | 6/2008 | Payne |
| 7,490,509 | B2 | 2/2009 | Bohmer |
| 7,614,298 | B2 | 11/2009 | Bohmer |
| 7,624,465 | B2 | 12/2009 | Oh |
| 7,744,298 | B2 | 6/2010 | Haas et al. |
| 8,101,408 | B2 | 1/2012 | Taylor et al. |
| 8,205,378 | B2 | 6/2012 | Banfield |
| 8,215,051 | B2 | 7/2012 | Alexander et al. |
| 8,215,065 | B2 | 7/2012 | Gallant |
| 8,440,009 | B2 | 5/2013 | Mahan |
| 8,501,247 | B2 | 8/2013 | Enan et al. |
| 8,522,488 | B1 | 9/2013 | Newkirk et al. |
| D692,089 | S | 10/2013 | Rubel et al. |
| 8,551,235 | B2 | 10/2013 | Mahan et al. |
| 8,707,615 | B2 | 4/2014 | Cullen |
| 8,852,501 | B2 | 10/2014 | Hedman |
| 2003/0056587 | A1 | 3/2003 | Carpenter et al. |
| 2003/0061758 | A1 | 4/2003 | Wilson |
| 2005/0132500 | A1 | 6/2005 | Karl et al. |
| 2005/0279033 | A1 | 12/2005 | Faber et al. |
| 2006/0270561 | A1 | 11/2006 | Keim et al. |
| 2007/0164059 | A1 | 7/2007 | Rosiello et al. |
| 2007/0193699 | A1 | 8/2007 | Repp et al. |
| 2007/0196412 | A1 | 8/2007 | Karl et al. |
| 2007/0289225 | A1 | 12/2007 | Kern et al. |
| 2008/0054020 | A1 | 3/2008 | Pierson et al. |
| 2008/0190088 | A1 | 8/2008 | Chou |
| 2008/0193387 | A1 | 8/2008 | De Wolff |
| 2009/0126257 | A1 | 5/2009 | Banfield |
| 2009/0222995 | A1 | 9/2009 | Perry et al. |
| 2009/0269381 | A1 | 10/2009 | Schilling et al. |
| 2010/0056656 | A1 | 3/2010 | Matsuoka et al. |
| 2010/0127224 | A1 | 5/2010 | Neff |
| 2010/0239679 | A1 | 9/2010 | Greene et al. |
| 2010/0260866 | A1 | 10/2010 | Lu |
| 2010/0264165 | A1* | 10/2010 | Hansen et al. ............... 222/95 |
| 2011/0124502 | A1 | 5/2011 | Enan |
| 2011/0135764 | A1 | 6/2011 | Enan |
| 2011/0236589 | A1 | 9/2011 | Streisfeld |
| 2011/0256198 | A1 | 10/2011 | Sonneck et al. |
| 2011/0311603 | A1 | 12/2011 | Lucas |
| 2012/0048145 | A1 | 3/2012 | Wang et al. |
| 2012/0167309 | A1 | 7/2012 | Heidorn |
| 2012/0227313 | A1 | 9/2012 | Mozeika, III et al. |
| 2012/0285076 | A1 | 11/2012 | Banfield |
| 2013/0025185 | A1 | 1/2013 | O'Connor |
| 2014/0041285 | A1 | 2/2014 | Russell et al. |
| 2014/0084774 | A1 | 3/2014 | Phillips |
| 2014/0259879 | A1 | 9/2014 | Logsdon |
| 2015/0007486 | A1 | 1/2015 | Backmark et al. |

FOREIGN PATENT DOCUMENTS

| | | |
|---|---|---|
| CA | 2163246 C | 2/2000 |
| CA | 2264383 A1 | 9/2000 |
| CN | 1550177 A | 12/2004 |
| CN | 2750730 Y | 1/2006 |
| CN | 200983804 Y | 12/2007 |
| CN | 201012152 Y | 1/2008 |
| CN | 101147643 A | 3/2008 |
| CN | 101381473 A | 3/2009 |
| CN | 201375245 Y | 1/2010 |
| CN | 201641161 U | 11/2010 |
| EP | 0412832 A2 | 2/1991 |
| EP | 2096141 A1 | 9/2009 |
| GB | 658221 | 10/1951 |
| GB | 673877 | 6/1952 |
| GB | 803611 A | 10/1958 |
| GB | 989014 | 4/1965 |
| GB | 998604 | 7/1965 |
| GB | 1521714 | 8/1978 |
| GB | 2107978 A | 5/1983 |
| GB | 2180449 A | 4/1987 |
| GB | 2370224 A | 6/2002 |
| GB | 2398007 A | 8/2004 |
| JP | 11-292704 A | 10/1999 |
| JP | 2000-176370 A | 6/2000 |
| WO | 9636220 A2 | 11/1996 |
| WO | 2009/017938 A1 | 2/2009 |
| WO | 2009045941 A1 | 4/2009 |
| WO | 2009058707 A1 | 5/2009 |
| WO | 2009117623 A2 | 9/2009 |
| WO | 2011/146663 A2 | 11/2011 |
| WO | 2012149636 A | 11/2012 |
| WO | 2013050967 A1 | 4/2013 |
| WO | 2013075212 A1 | 5/2013 |
| WO | 2013101298 A1 | 7/2013 |
| WO | 2013160898 A1 | 10/2013 |

OTHER PUBLICATIONS

The benefits of Diatomaceous earth accessed at http://www.offthegridnews.com on Jun. 30, 2014.*
International Search Report mailed Feb. 13, 2013, from PCT Application No. PCT/CA2012/001015 (4 pages).
International Preliminary Report on Patentability mailed Nov. 14, 2013, from PCT Application No. PCT/CA2012/000389 (6 pages).
International Search Report mailed Aug. 8, 2012, from PCT Application No. PCT/CA2012/000389 (4 pages).
Aerosol tops 6, downloaded from http://en.wikipedia.org/wiki/File:Aerosol_tops_6.svg, Mar. 6, 2007.
Agrium Advanced Technologies, Material Data Safety Sheet, PRO® Green Earth S. D. Insect Dust, Nov. 2010.
Akhtar et al., Horizontal Transfer of Diatomaceous Earth and Botanical Insecticides in the Common Bed Bug, Cimex lectularius L.; Hemiptera: Cimicidae, Sep. 25, 2013, PLoS One 8(9): e75626. doi:10.1371/journal.pone.0075626.
Akhtar, Toxicity data for De 51 and DE 53 against bed bugs, Jun. 23, 2011.
American Diatomite Inc., downloaded from http://www.americandiatomite.com/ on Apr. 12, 2014, NV, USA.

(56) References Cited

OTHER PUBLICATIONS

Available Products, Diatomaceous Earth Hawaii, downloaded from http://www.diatomaceousearthhawaii.com/available-products.html on Jun. 26, 2012.
Bacillariophyceae Algae, downloaded from http://web.biosci.utexas.edu/utex/algaeDetail.aspx?algaeID=6184, Apr. 5, 2006, University of Texas at Austin, Austin, TX, USA.
BadBedBugs.com, Bed Bug Dust: Diatomaceous Earth (DE) is a Natural Solution You Can Buy Anywhere, 2008-2014, downloaded from http://www.badbedbugs.com/bed-bug-dust/ on Jan. 4, 2014.
Barrentine, New—Oa2ki (DE) in a can!!, from http://www.barrettine.co.uk/Environmental-Health/index.php?option=com_content&view=article&id=92:oa2ki-aerosol&catid=1:latest-news&Itemid=18 and dated Oct. 24, 2011 on http://web.archive.org/, Barrentine, United Kingdom.
BASF, The Chemical Company, Better Products for Pest Control Product List, BASF The Chemical Company, USA, downloaded from http://pestcontrol.basf.us/products/product-index.html on Mar. 19, 2012.
Berg, Bed bugs: The pesticide dilemma, Journal of Environmental Health, Jun. 1, 2010, pp. 32-35, vol. 72, National Environmental Health Association, Denver, CO, USA.
Canada, MotherEarth D Pest Control Dust, Nov. 22, 2012, Pest Management Regulatory Agency, Canada.
Canadian Center for the Culture of Microorganisms, downloaded from http://www3.botany.ubc.ca/cccm/, May 28, 2001, University of British Columbia, Vancouver, BC, Canada.
Diafil 610, EPA Reg. No. 73729-1, Feb. 13, 2003.
DiaSource Diatomaceous Earth, EPA Reg. No. 69261-5, Dec. 16, 2010.
Diatomaceous Earth Hawaii, downloaded from http://www.diatomaceousearthhawaii.com/ on Jun. 26, 2012.
Domingue et al., Sexual dimorphism of arrestment and gregariousness in the bed bug (Cimex lectularius) in response to cuticular extracts from nymphal exuviae, Physiological Entomology, Sep. 2010, pp. 203-213, vol. 35, Issue No. 3, Wiley, Hoboken, NJ, USA.
Eagle-Picher Minerals, Inc., Crop Guard™, EPA Reg. No. 007655-1, Jan. 11, 1995, Reno, NV, USA.
Ecosmart, Bed Bugs, downloaded from http://ecosmart.com/bed-bugs/ on Mar. 6, 2014, EcoSmart Technologies, Roswell, GA, USA.
EP Minerals, Celatom® FN & MN Grades, Material Safety Data Sheet, Jun. 10, 2010, EP Minerals, Reno, NV, USA.
EP Minerals, Celatom® MN-51, Technical Data Sheet, Oct. 2010, EP Minerals, Reno, NV, USA.
EP Minerals, Celatom® MN-53, Technical Data Sheet, Oct. 2010, EP Minerals, Reno, NV, USA.
Gagne et al., Questions on Registration Requirements for an End-use Diatomaceous Earth Product, 2013.
Harlan, Bed Bugs 101: the Basics of Cimex lectularius., American Entomologist, 2006, pp. 99-101, vol. 52, No. 2, Entomological Society of America, Annapolis, MD, USA.
Haynes et al., Bed bug deterrence, BMC Biology, Sep. 9, 2010, pp. 117-119, vol. 8, BioMed Central, Lexington, KY, USA.
Health Canada, Diatomaceous Earth in Aerosol, Pesticide Label Search, Feb. 15, 2012, Government of Canada, Canada.
Hopkins et al., Fresh Water, Food-Grade Diatomaceous Earth, 2004-2011, Best Prices Storable Foods, Quinlan, TX, USA, cited in International Search Report dated Feb. 13, 2013 in PCT/CA2012/001015 as being dated Oct. 25, 2011 at http://web.archive.org/web/2011102562102/http://www.internet-grocer.net/diatome.htm.
Hopkins et al., Fresh Water, Food-Grade Diatomaceous Earth, 2004-2011, Best Prices Storable Foods, Quinlan, TX, USA, downloaded from http://www.internet-grocer.net/diatome.htm on Oct. 31, 2011.
Isman et al., Quantitative Phase Analysis of Diatomaceous Earth Using the Rietveld Method and X-Ray Powder Diffraction Data. Scanning Electron Microscope Images of Diatomaceous Earth, May 2, 2012, University of British Columbia, Vancouver, BC, Canada.
Isman et al., Quantitative Phase Analysis of Diatomaceous Earth Using the Rietveld Method and X-Ray Powder Diffraction Data. Scanning Electron Microscope Images of Diatomaceous Earth, May 22, 2012, University of British Columbia, Vancouver, BC, Canada.
Isman et al., Scanning Electron Microscope Images of Diatomaceous Earth, Jul. 16, 2012, University of British Columbia, Vancouver, BC, Canada.
Isman et al., Toxicity of different types of diatomaceous earth against the common bed bug, Cimex lectularius in the laboratory, Apr. 30, 2012, University of British Columbia, Vancouver, BC, Canada.
Isman, Residual toxcity of aerosol (51) against bed bugs, Feb. 1, 2012, University of British Columbia, Vancouver, BC, Canada.
Isman, Toxicity data for dust samples, Jul. 17, 2012, University of British Columbia, Vancouver, BC, Canada.
Isman, Toxicity data of different dusts, Feb. 18, 2012, University of British Columbia, Vancouver, BC, Canada.
JP Textiles, Headboards—Upholstered, Pricelist, 2008, JP Textiles, Vancouver, BC, Canada.
K-G Spray-Pak Inc, Gravimetric Determination of Solids Concentration (percent active) in JP Bed Bug Killer, Jun. 20, 2012.
Kobylnyk, Similar Registered Product, Nov. 21, 2011.
Korunic, Diatomaceous Earths, a Group of Natural Insecticides, Journal of Stored Products Research, 1998, pp. 87-97, vol. 34, Issue No. 2-3, Elsevier Science, United Kingdom.
Korunic, Rapid Assessment of the Insecticidal Value of Diatomaceous Earths Without Conducting Bioassays, Journal of Stored Products Research, 1997, pp. 219-229, vol. 33, No. 3, Elsevier Science, United Kingdom.
Malvern Instruments, EP51 Result Analysis Report, Oct. 30, 2012, Malvern Instruments Ltd., Malvern, UK.
Malvern Instruments, Mother Earth Result Analysis Report, Oct. 30, 2012, Malvern Instruments Ltd., Malvern, UK.
McGrath, Is Diatomaceous Earth Harmful?, Demand Media, USA, 1999-2013, downloaded from http://www.ehow.com/about_6571034_diatomaceous-earth-harmful_.html on Nov. 7, 2013.
Moore et al., Laboratory Evaluations of Insecticide Product Efficacy for Control of Cimex lectularius, Journal of Economic Entomology, Dec. 2006, pp. 2080-2086, vol. 99, No. 6, Entomological Society of America, Annapolis, MD, USA.
One Stop Grow Shop, Crop Guard—DustOff PM 250Mls, downloaded from http://www.onestopgrowshop.co.uk/pest-and-disease-control/leaf-and-flower-mould-rot-control-en/crop-guard-dustoff-pm-250mls.html on Apr. 18, 2014, Stoke-on-Trent, Staffordshire, UK.
Pereira, Lethal effects of heat and use of localized heat treatment for control of bed bug infestations, Journal of Economic Entomology, Jun. 2009, pp. 1182-1188, vol. 102, No. 3, Entomological Society of America, Annapolis, MD, USA.
Pest Control Direct, Oa2ki Aerosol Pesticide Free Ant Killer Powder, United Kingdom, downloaded from http://www.pestcontroldirect.co.uk/acatalog/0a2ki_Aerosol_500gm_Powder_in_a_Can_.html on Oct. 31, 2011.
Pest Control Direct, Pest Control Direct Reviews, United Kingdom, downloaded from http://www.feefo.com/GB/en/reviews/Pest-Control-Direct/?id=103607 on Oct. 31, 2011.
Pesticide Action Network, Crop guard, downloaded from http://www.pesticideinfo.org/Detail_Product.jsp?REG_NR=00765500001&DIST_NR=007655 on Apr. 8, 2014.
Power, Examination of sample EP51 by scanning electron microscopy, Aug. 9, 2012, University of British Columbia, Vancouver, BC, Canada.
ProGreen S.D. Insect Dust Label Notification Change, 2007-2008.
Reinhardt et al., Biology of the Bed Bugs (Cimicidae), Annual Review of Entomology, Sep. 1, 2006, pp. 351-374, vol. 52, Annual Reviews, Palo Alto, CA, USA.
Romero et al., Insecticide Resistance in the Bed Bug: A Factor in the Pest's Sudden Resurgence?, Journal of Medical Entomology, Mar. 2007, pp. 175-178, vol. 44, Entomological Society of America, Annapolis, MD, USA.
Sacred Mountain, Diatomaceous Earth, Sacred Mountain, Visalia, CA, USA, downloaded from http://sacredmountainjourney.com/id21.html on Nov. 7, 2013.
Synedra delicatissima sensu PR, downloaded from http://craticula.ncl.ac.uk/Eddi/jsp/showimage.jsp?TaxonId=XXG987 on Mar. 5, 2014, Newcastle University, United Kingdom.

(56) References Cited

OTHER PUBLICATIONS

The Company's Beginnings, Diatomaceous Earth Hawaii, downloaded from http://www.diatomaceousearthhawaii.com/the-companys-beginnings.html on Jun. 26, 2012.
Todd, Repellents for Protection from Bed Bugs: The Need, the Candidates, Safety Challenges, Test Methods and the Chance of Success, Recent Developments in Invertebrate Repellents, 2011, pp. 137-150, Chapter 9, ACS Publications, Washington, DC, USA.
Tui Rose, Going Green Using Diatomaceous Earth How-to-Tips, 2012, downloaded from http://www.tuirose.com/diatomaceous-earth-book-introduction.php on Nov. 7, 2013.
UTEX The Culture Collection of Algae, downloaded from http://web.biosci.utexas.edu/utex/ on Mar. 5. 2014, University of Texas at Austin, Austin, TX, USA.
Vayias et al., Evaluation of natural diatomaceous earth deposits from south-eastern Europe for stored-grain protection: the effect of particle size, published online Jun. 18, 2009, Pest Management Science, pp. 1118-1123, vol. 65, Society of Chemical Industry.
Wang et al., Case Study: Controlling Bed Bugs in Apartments, Pest Control Technology, Nov. 2007, pp. 64-70, vol. 35, GIE Media, Richfield, OH, USA.
Watson, The Brutal Business of Battling Bedbugs, Sep. 12, 2010, Daily Finance, USA, downloaded from http://www.dailyfinance.com/2010/09/12/the-business-of-bedbugs/ on Apr. 19, 2011.
Weeks et al., A bioassay for studying behavioural responses of the common bed bug, *Cimex lectularius* (Hemiptera: Cimicidae) to bed bug-derived volatiles, Bulletin of Entomological Research, Jan. 27, 2010, pp. 1-8, vol. 101, Cambridge University, Cambridge, UK.
What is Diatomaceous Earth ( DE )?, Diatomaceous Earth Hawaii, downloaded from http://www.diatomaceousearthhawaii.com/what-is-diatomaceous-earth--de.html on Jun. 26, 2012.
Whitmire Micro-Gen Research Laboratories, Inc., Prescription Treatment® brand TRI-DIE®, 2005, St. Louis MO, USA.
Whitmire PT® 239 Tri Die Insecticide, EPA Registration No. 499-385, Aug. 29, 2013.
Power, Review of Diatomaceous Earths in Table 3 of Korunic, a Group of Natural Insecticides, 1998, University of British Columbia, Vancouver, BC, Canada (2 pages).
Extended European Search Report mailed Sep. 2, 2014, from European Application No. 12779394.1 (5 pages).
Diatomaceous Earth General Fact Sheet, National Pesticide Information Center, retrieved from http://npic.orst.edu/factsheets/degen.html on Jan. 27, 2015, 4 pages.
First Office Action mailed Mar. 27, 2015, from Chinese Application No. 201280021613.2 (10 pages).
Doggett, Stephen L. et al., "The efficacy of diatomeous earth against the common Bed Bug, Cimex Lectularíus: A report for Mount Sylvia Diatomite," May 1, 2008, pp. 1-50, XP055205184, Retrieved from the Internet on Jul. 29, 2015 at http://mtsylviadiatomite.com.au/mod/files/documents/Final_bedbug_trial.pdf.
Mann, David G., "Raphid diatoms", Tree of Life Web Project, Feb. 7, 2010, pp. 1-4, XP055205449, Retrieved from the Internet Jul. 30, 2015 at http://tolweb.org/raphid_diatoms/125307.
Extended European Search Report mailed Aug. 11, 2015, from European Application No. 12850927.0 (10 pages).
Wang, Jingshing, "Diatomite Using Insecticide," p. 22, Jul. 1999. Foreign Article. Retrieved from the Internet in Oct. 2015 at http://www.cnki.net.
Chen, Jiannen, "Introduction of a Introduction of a Novel Physical Insecticide (PG)," pp. 21 and 38, Jan. 1995. Foreign Article. Retrieved from the Internet in Oct. 2015 at http://www.cnki.net.

\* cited by examiner

SPRAY APPARATUSES, USES OF DIATOMACEOUS EARTH, AND METHODS OF CONTROLLING INSECT POPULATIONS

RELATED APPLICATIONS

This application is a continuation of and claims the benefit of PCT international patent application no. PCT/CA2012/001015, filed on Nov. 1, 2012. PCT international patent application no. PCT/CA2012/001015, filed on Nov. 1, 2012, claims the benefit of U.S. provisional patent application No. 61/563,220 filed on Nov. 23, 2011, and the benefit of PCT international patent application no. PCT/CA2012/000389 filed at the Canadian receiving office of the PCT on Apr. 26, 2012. PCT international patent application no. PCT/CA2012/000389 was filed as U.S. National Phase application Ser. No. 14/114,900 on Oct. 30, 2013. The entire contents of PCT international patent application no. PCT/CA2012/001015, filed on Nov. 1, 2012, U.S. provisional patent application No. 61/563,220 filed on Nov. 23, 2011, PCT international patent application no. PCT/CA2012/000389 filed at the Canadian receiving office of the PCT on Apr. 26, 2012, and U.S. application Ser. No. 14/114,900 filed on Oct. 30, 2013, are incorporated by reference herein.

BACKGROUND

1. Field

The invention relates generally to insect population control, and more particularly to spray apparatuses, uses of diatomaceous earth, and methods of controlling insect populations.

2. Related Art

Many insects, such as the insects commonly known as "bedbugs" for example, have become pests in many parts of the world. A bedbug infestation of a building, for example, can be very costly, because often furniture must be destroyed and replaced in order to remove bedbugs from the building. Further, in the case of some institutions such as hotels for example, closing large parts or all of the hotel for bedbug pest removal can result in significant loss of revenue.

Some known methods of controlling bedbug populations involve using synthetic pesticides, but some pesticides may be harmful to humans and to other life. Other known methods of controlling bedbug populations include applying diatomaceous earth, a naturally occurring siliceous sedimentary rock that includes fossilized remains of diatoms.

However, known methods of applying diatomaceous earth can be cumbersome. For example, known methods of applying diatomaceous earth may undesirably require handling the diatomaceous earth, for example to transfer the diatomaceous earth from a container not having an applicator to a separate applicator apparatus. Also, known applicator apparatuses may apply diatomaceous earth unevenly, which may be wasteful or ineffective. In general, known methods of applying diatomaceous earth may be sufficiently complex so as to require professional involvement, which may undesirably add to cost and delay of bedbug treatment.

Also, numerous types of diatomaceous earth are available, and different types of diatomaceous earth vary widely and significantly from each other. It has been estimated that there are approximately 100,000 extant diatom species, and some diatomaceous earth may also include diverse combinations of one or more diatom species and may also include extinct species in addition to the number of extant species. Diatom skeletons (which may also be referred to as "frustules") may vary widely and significantly in size and shape across a very large number of diatom species. Also, different insect species have different bodies that may be affected significantly differently by different types of diatomaceous earth. Therefore, many varieties of diatomaceous earth are available, and a variety of diatomaceous earth that is effective at controlling a population of one type of insect may not be as effective, or effective at all, at controlling a population of another type of insect.

SUMMARY

According to one illustrative embodiment, there is provided a spray apparatus comprising: a means for holding contents comprising diatomaceous earth and a compressed propellant for propelling the diatomaceous earth from the means for holding; and a means for controllably releasing the propellant and the diatomaceous earth propelled by the propellant from the means for holding.

According to another illustrative embodiment, there is provided a spray apparatus comprising: a body defining a reservoir holding contents comprising diatomaceous earth and a compressed propellant for propelling the diatomaceous earth from the reservoir; and an actuator for controllably releasing the propellant and the diatomaceous earth propelled by the propellant from the reservoir.

According to another illustrative embodiment, there is provided use of diatomaceous earth to control a population of bedbugs, wherein the diatomaceous earth comprises remains of pennate diatoms.

According to another illustrative embodiment, there is provided use of diatomaceous earth to control a population of *Cimicidae*, wherein the diatomaceous earth comprises remains of pennate diatoms.

According to another illustrative embodiment, there is provided use of diatomaceous earth to control a population of *Cimex*, wherein the diatomaceous earth comprises remains of pennate diatoms.

According to another illustrative embodiment, there is provided use of diatomaceous earth to control a population of *Cimex lectularius*, wherein the diatomaceous earth comprises remains of pennate diatoms.

According to another illustrative embodiment, there is provided a method of controlling a population of bedbugs, the method comprising exposing the bedbugs to diatomaceous earth comprising remains of pennate diatoms.

According to another illustrative embodiment, there is provided a method of controlling a population of *Cimicidae*, the method comprising exposing the *Cimicidae* to diatomaceous earth comprising remains of pennate diatoms.

According to another illustrative embodiment, there is provided a method of controlling a population of *Cimex*, the method comprising exposing the *Cimex* to diatomaceous earth comprising remains of pennate diatoms.

According to another illustrative embodiment, there is provided a method of controlling a population of *Cimex lectularius*, the method comprising exposing the *Cimex lectularius* to diatomaceous earth comprising remains of pennate diatoms.

According to another illustrative embodiment, there is provided a method of controlling a population of insects, the method comprising causing a compressed propellant to propel diatomaceous earth on a surface.

According to another illustrative embodiment, there is provided a method of manufacturing a spray apparatus, the method comprising adding a smaller size fraction of diatomaceous earth to the spray apparatus.

According to another illustrative embodiment, there is provided a method of preparing diatomaceous earth for use in controlling a population of insects, the method comprising size separating the diatomaceous earth into a smaller size fraction and into a larger size fraction.

Other aspects and features of the present invention will become apparent to those ordinarily skilled in the art upon review of the following description of illustrative embodiments in conjunction with the accompanying figures.

DETAILED DESCRIPTION

A. Spray Apparatus

Figure 1:
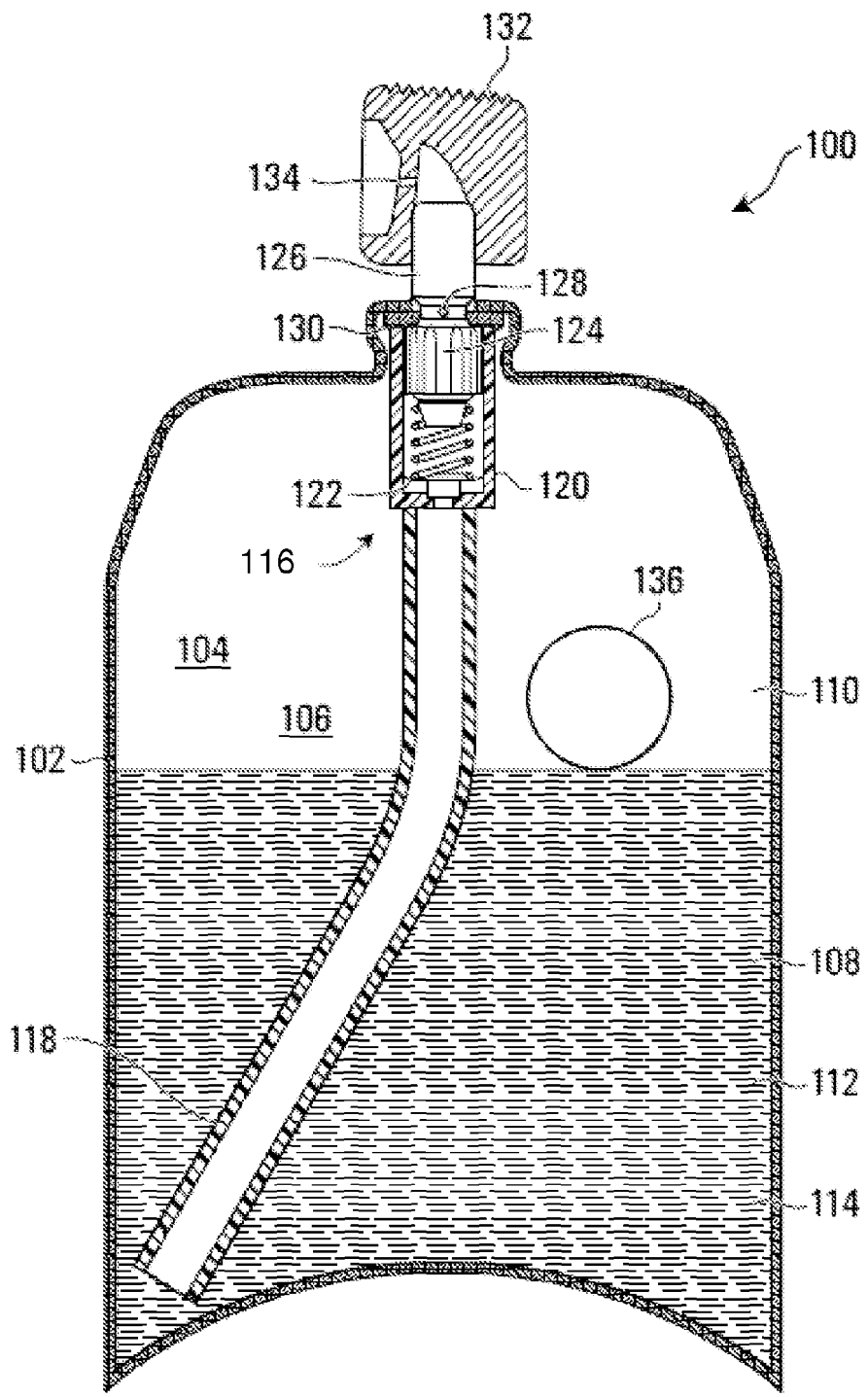
FIG. 1 is a cross-sectional view of a spray apparatus according to one illustrative embodiment.
Figure 2:
FIGS. 2 to 5 are secondary electron images of diatomaceous earth known as CELATOM™ MN-51.

Referring to FIG. 1, a spray apparatus according to one illustrative embodiment is shown generally at 100. U.S. Pat. Nos. 6,394,321 and 6,581,807 describe aerosol containers that may be suitable for spraying powder, and in some embodiments the spray apparatus 100 may be similar to one of the aerosol containers described and illustrated in U.S. Pat. Nos. 6,394,321 and 6,581,807 or to other aerosol containers that may be suitable for spraying powder.

The spray apparatus 100 in the embodiment shown includes a body 102 defining a reservoir 104 therein. The body 102 may include a steel can, and the body 102 in the embodiment shown is thus a rigid container. Alternative embodiments may include or other material suitable, such as other rigid containers for example, for holding pressurized air. For example, the body 102 in one embodiment may be a steel can having a size known to one skilled in the art as "202×509" (or 2 3/16 inches in diameter and 5 9/16 inches in height, or about 5.4 centimeters ("cm") in diameter and about 14.1 cm in height) and having an inner epoxy coating, and which may be sized so that the reservoir 104 holds 170 grams of contents 106. The body 102 thus holds the contents 106, although alternative embodiments may include different structures to hold the contents 106. For example, in some embodiments, the body 102 may include a tin-plated steel can with a protective liner.

In the embodiment shown, the contents 106 include diatomaceous earth 108 and a propellant, which in some embodiments may be a mixture of isobutane and propane known to one skilled in the art as propellant A-46, and which in some embodiments may include about 75% isobutane and about 25% propane. In other embodiments, the propellant may be a liquefied petroleum gas known to one skilled in the art as propellant blend A-70 available from Brenntag Canada Inc. of Toronto, Ontario, Canada. In the embodiment shown, the propellant is in a gaseous phase 110, and also in a liquid phase 112 intermixed with the diatomaceous earth 108. Further, the contents 106 in the embodiment shown include an unmatured anhydrous alcohol 114 intermixed with the diatomaceous earth 108. The alcohol 114 may be denatured with fragrance, resin, a product known as BITREX™, or another product for example. The alcohol 114 may include an alcohol known to one skilled in the art as SD-40 or SDAG-6, for example. In some embodiments, such alcohol 114 may evaporate generally rapidly one sprayed from the spray apparatus 100, thereby leaving dried diatomaceous earth 108 on a surface (not shown) sprayed by the spray apparatus 100.

In the embodiment shown, the alcohol 114 is about 54% by weight of the contents 106, the propellant is about 38% by weight of the contents 106, and the diatomaceous earth 108 is about 8% by weight of the contents 106. In other embodiments, the diatomaceous earth 108 may be at least 3% by weight of the contents 106, at least 5% by weight of the contents 106, or at least 7% by weight of the contents 106, for example, and in such embodiments the propellant may be more than about 38% by weight of the contents 106 and/or the alcohol 114 may be more than about 54% by weight of the contents 106.

In still other embodiments, products other than diatomaceous earth, such as other products that may be effective to control bedbug populations or more generally as an insecticide or pesticide for example, may be intermixed with the diatomaceous earth 108. For example, U.S. Pat. No. 8,101,408 describes various legume extracts, such as one or more of PA1b-related peptides, terpenoid saponins, triterpenoid saponin, soyasaponin I, soyasaponin II, soyasaponin III, soyasaponin VI, dehydrosoyasaponin I, echinocystic acid 3-glucoside, glycyrrhizic acid, hederacoside C, beta-escin, alpha-hederin, and other acetic acid precipitated insecticidal components. In various embodiments, such legume extracts may be intermixed with the diatomaceous earth 108, and in such embodiments the propellant may be less than about 38% by weight of the contents 106 and/or the alcohol 114 may be less than about 54% by weight of the contents 106.

One skilled in the art will appreciate that the contents 106 need not be exactly in the aforementioned proportions, that the spray apparatus 100 may function similarly with more or less of those components, and that "about" in this context means refers to variations of the aforementioned proportions that allow the spray apparatus 100 to function with similar results.

The spray apparatus 100 also includes an aerosol valve assembly shown generally at 116 and including a tube 118, a valve housing 120 receiving the tube 118 at the bottom of the valve housing 120, a valve-closing coil spring 122, and a valve body 124 having a hollow valve stem 126 defining lateral openings 128 extending into the interior of the valve stem 126. A gasket 130 surrounds the valve stem 126 and seals the openings 128 when the aerosol valve is closed. An actuator 132 is attached to the top of the valve stem 126 such that an outlet nozzle 134 of the actuator 132 is in fluid communication with the interior of the valve stem 126.

Further, the reservoir 104 includes a ball bearing or marble 136 to facilitate mixing the contents 106 when the spray apparatus 100 is shaken. For example, in one embodiment, the spray apparatus 100 may be shaken for about 8 to about 10 seconds, or vigorously for about 10 seconds, to achieve desirable mixing of the contents 106 before the contents 106 are sprayed from the spray apparatus 100.

One skilled in the art will appreciate numerous variations from the spray apparatus 100. For example, alternative embodiments may include various alternative cans, valves, and actuators. For example, one embodiment may include a valve suitable for power and coated on a top side to prevent rusting, such as a valve known to one skilled in the art as Prec. powder valve S.2X.020 Ringed Barb 630 (OAL) (04-0519-42) G.Hex Buna B175 B.080x.030VT 412 Deep MC con. Epon Top Lam. Bot dimp. DT 138 mm A-D, and an actuator known to one skilled in the art as Act.025" NMBU Raised APSL 0.022 White (21-9116-00-0343). Various embodiments may also include a cap (not shown) to protect the actuator from being actuated unintentionally, such as during shipping for example. Alternative embodiments may also include different contents, such as different propellants for example.

Some embodiments of the spray apparatus 100 or alternative embodiments may be prepared by a batch process. The description below is one example of a manufacturing process for 1,000 kilograms of formulated product. First, 540 kilograms of anhydrous ethyl alcohol is held in a clean and dry stainless steel tank, and 80 kilograms of diatomaceous earth powder is then added slowly (to avoid clumping) to the anhydrous ethyl alcohol under medium mixing using an air mixer until homogeneous to form a bulk concentrate of 620 kilograms. The mixing may require about 15 minutes. Then, portions of the bulk concentrate are metered through a filter into aerosol containers at a temperature between 68° F. (about 20° C.) and 73° F. (about 22.8° C.). For an aerosol container having a size known to one skilled in the art as "211×604" (or 2$^{11}$/$_{16}$ inches in diameter and 6$^{4}$/$_{16}$ inches in height, or about 6.8 cm in diameter and about 15.9 cm in height), 186 grams of bulk concentrate may be added, and for an aerosol container having a size known to one skilled in the art as "211×713" (or 2$^{11}$/$_{16}$ inches in diameter and 7$^{13}$/$_{16}$ inches in height, or about 6.8 cm in diameter and about 19.8 cm in height), 248 grams of bulk concentrate may be added.

Each aerosol container may then be fitted with an aerosol valve and subjected to a vacuum at 15 inches of mercury (about 50.8 kilopascals) to 20 inches of mercury (about 67.7 kilopascals). The propellant (A-70 in this example) may then be metered under pressure into each aerosol container at a temperature between 65° F. (about 18.3° C.) and 70° F. (about 21.1° C.) and at a pressure of 600 pound-force per square inch gauge (about 4,238 kilopascals) to 650 pound-force per square inch gauge (about 4,583 kilopascals), and each aerosol container may be then crimped shut.

For an aerosol container having a size known to one skilled in the art as "211×604" (or 2$^{11}$/$_{16}$ inches in diameter and 6$^{4}$/$_{16}$ inches in height, or about 6.8 cm in diameter and about 15.9 cm in height), 114 grams of propellant may be added, and for an aerosol container having a size known to one skilled in the art as "211×713" (or 2$^{11}$/$_{16}$ inches in diameter and 7$^{13}$/$_{16}$ inches in height, or about 6.8 cm in diameter and about 19.8 cm in height), 152 grams of propellant may be added.

The aerosol containers may then be placed in a hot water bath of 130° F. (about 54° C.) to 140° F. (about 60° C.) for about 30 seconds to test the strength of the aerosol containers. An outer cap, a label, and lot number may then be placed on each aerosol container, and the aerosol containers may be packaged in boxes for distribution. The label may include precautionary information, such as markings not to use the aerosol container in the presence of an open flame or a spark, or while smoking, a warning that the aerosol container may explode if heated, a warning not to expose to temperatures above 50° C. or 122° F., and a warning not puncture or incinerate for example.

In operation, when the actuator 132 is pressed towards the body 102 against the force of the spring 122, the openings 128 pass below the gasket 130 to open controllably the openings 128 and thus controllably allow the contents 106 pass through the tube 118, through the openings 128, into the valve stem 126, into the actuator 132, and to be sprayed out the nozzle 134 under pressure from the propellant. When the actuator 132 is released, the spring 122 urges the valve stem 126 to the a position where the openings 128 are blocked by the gasket 130 to close the aerosol valve and prevent the contents 106 from entering into the valve stem under pressure from the propellant. Therefore, the nozzle 134 may controllably release the propellant, and the diatomaceous earth 108 propelled by the propellant, from the reservoir 104.

B. Diatomaceous Earth Products

Numerous types of diatomaceous earth are available and vary, for example, on the sizes, shapes, and species of diatoms that contributed to the diatomaceous earth.

1. CELATOM™ MN-51

The diatomaceous earth 108 in some embodiments may include CELATOM™ MN-51, which is available from EP Minerals, LLC of 9785 Gateway Drive, Suite 1000, Reno, Nev., United States of America. The diatomaceous earth known as CELATOM™ MN-51 is believed to be a food-grade diatomaceous earth that originates from a deposit formed from fresh-water diatoms at Clark Station, Nev., United States of America, and that may be heat-treated or flash dried at about 900° F. (about 480° C.) or at other temperatures, for example. In one embodiment, flash drying diatomaceous earth involves heating the diatomaceous earth at about 900° F. (about 480° C.) for about 15 seconds.

Figure 3:
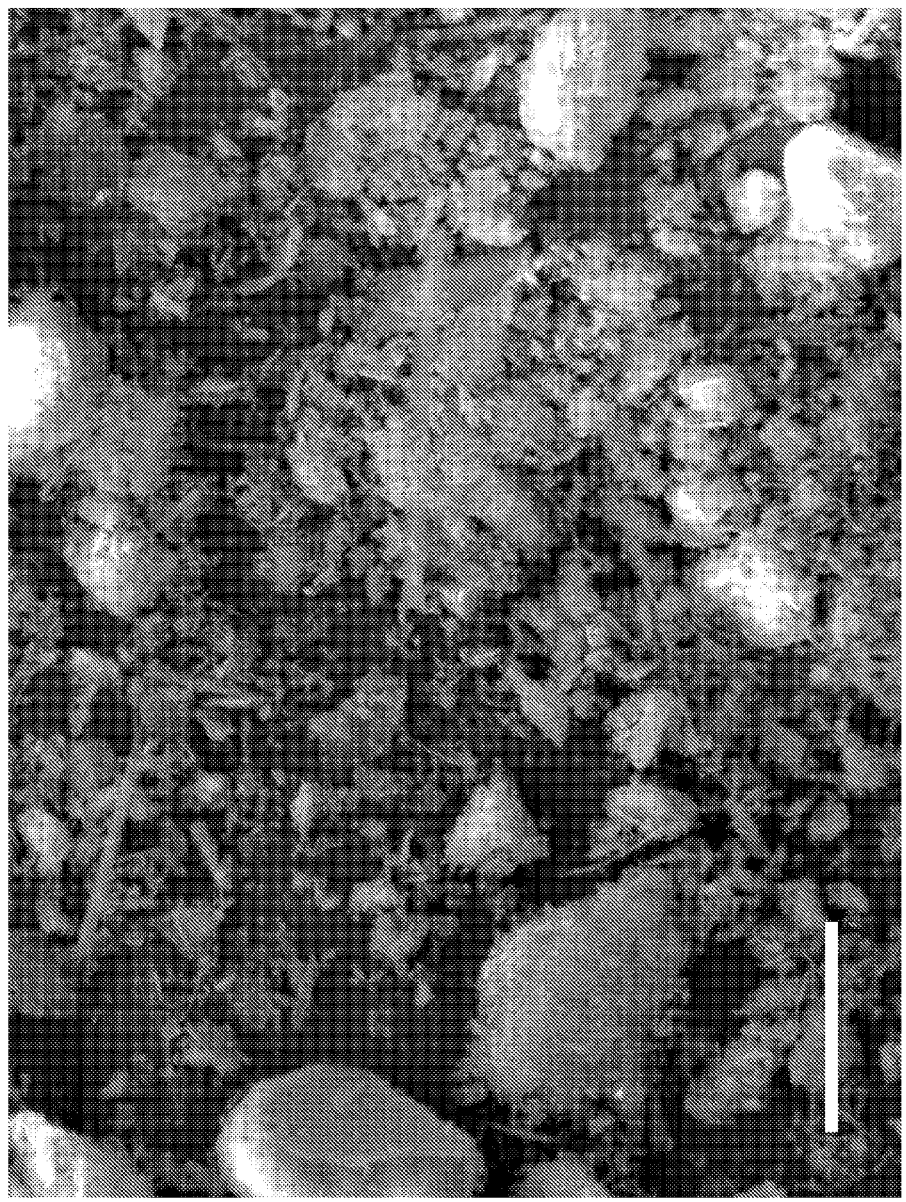
Figure 4:
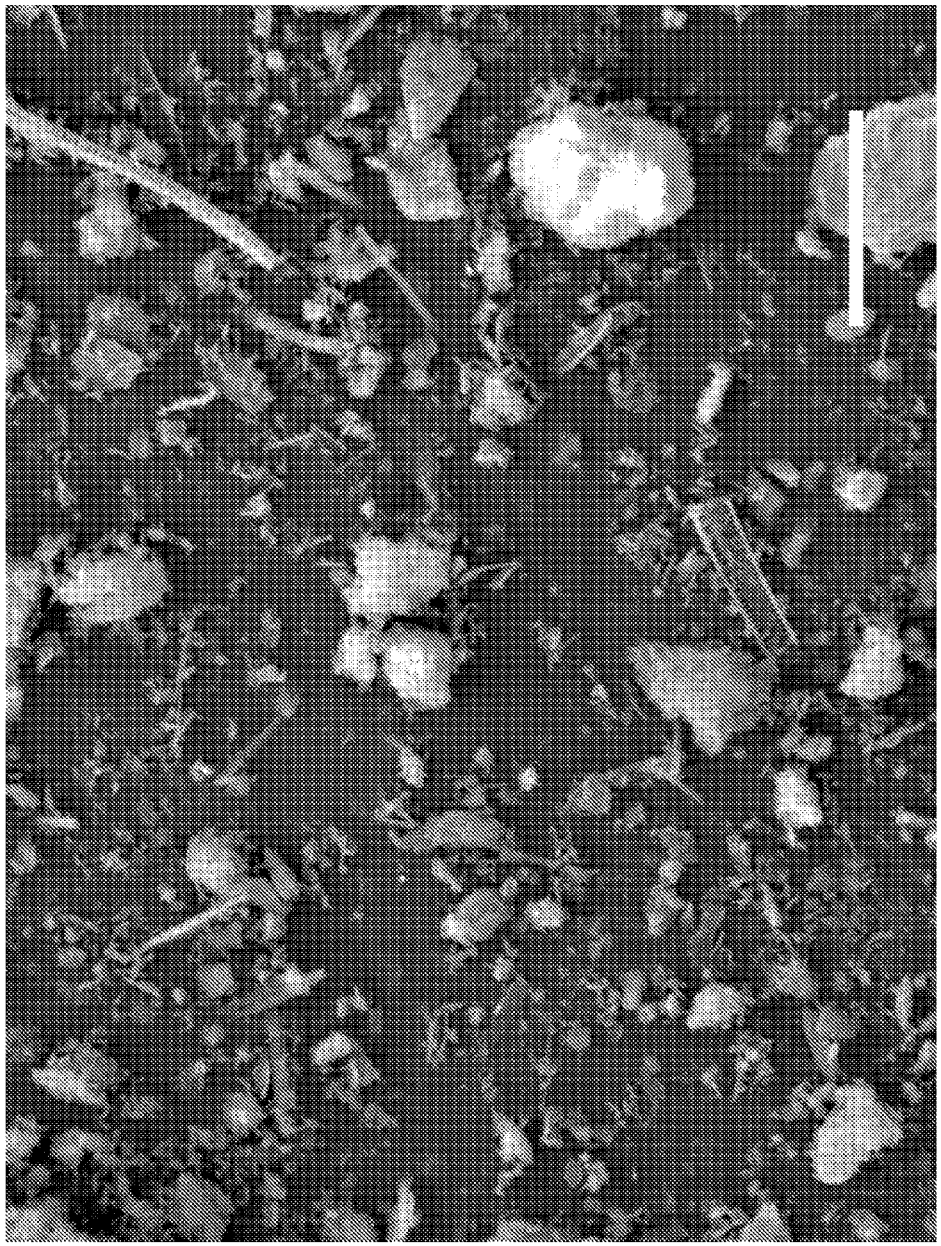
Figure 5:
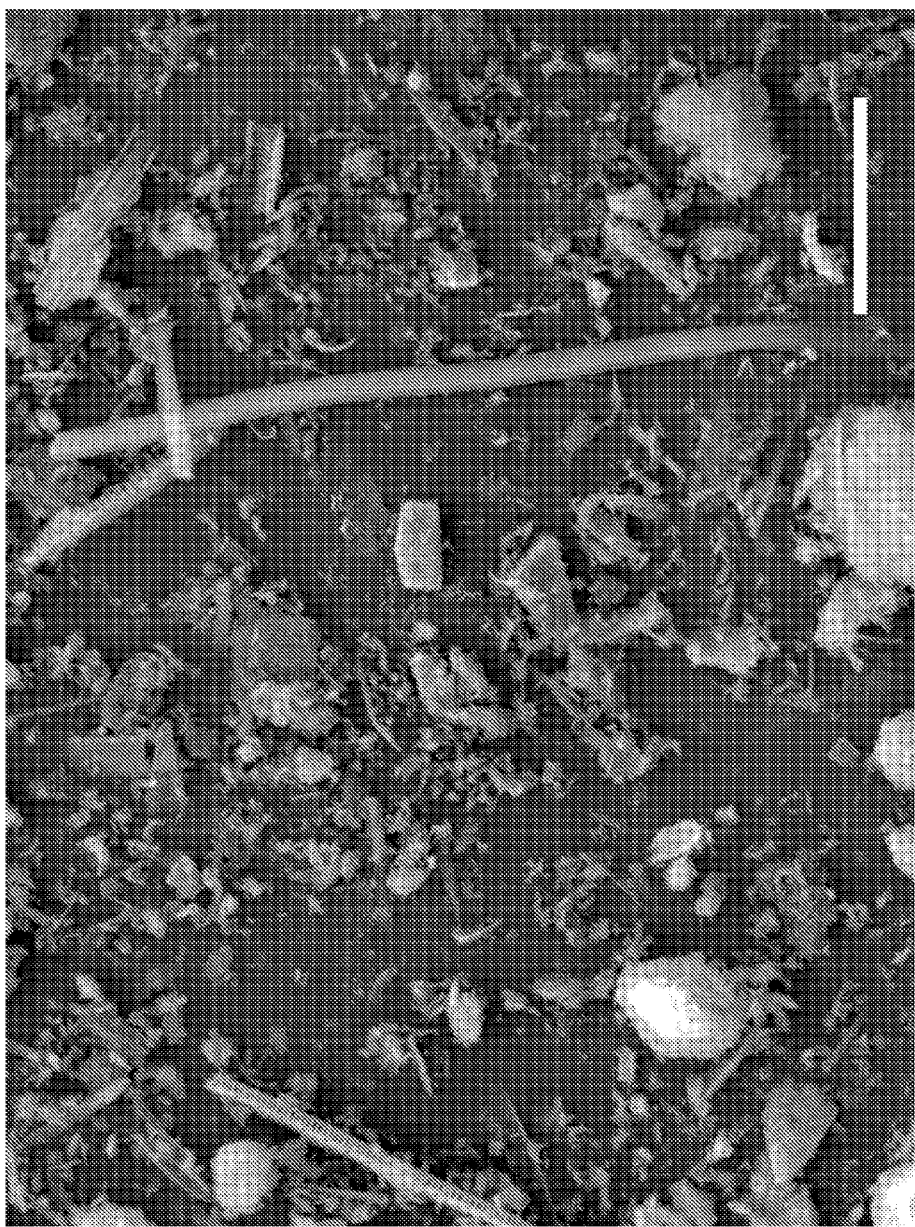

FIGS. 2 to 5 are secondary electron images (using a Philips XL-30 scanning electron microscope after coating with evaporated gold) of the diatomaceous earth known as CELATOM™ MN-51. The scale bars in FIGS. 3 to 5 represent 30 micrometers in those Figures.

The diatomaceous earth known as CELATOM™ MN-51 is believed to have the properties given in Table 1 below.

TABLE 1

| Properties of CELATOM ™ MN-51. | |
|---|---|
| Structure | Natural |
| Color | Beige |
| G.E. Brightness | 75 |
| Sieve Analysis (Tyler) % + 325 Mesh (>44 microns) | 6.5 |
| Median Particle Diameter (microns) | 15.0 |
| pH (10% slurry) | 7.5 |
| Free Moisture | |
| (Maximum % H$_2$O) | Less than 5.0 |
| (Typical % H$_2$O) | 3.0 |

TABLE 1-continued

Properties of CELATOM ™ MN-51.

| Density | (lb/ft³) | (g/l) |
|---|---|---|
| Wet Bulk | 24 | 385 |
| Dry Bulk | 11 | 176 |
| Specific Gravity | 2.00 | |
| Refractive Index | 1.46 | |
| Oil Absorption (ASTM F 726-81) % by weight | 150 | |
| Water Absorption (ASTM F 726-81) % by weight | 165 | |
| Chemical Analysis | | |
| $SiO_2$ | 73.6% | |
| $Al_2O_3$ | 7.8% | |
| $Fe_2O_3$ | 1.8% | |
| CaO | 5.6% | |
| MgO | 0.3% | |
| Other Oxides | 2.3% | |
| Loss on Ignition | 5.5% | |

A sample of the diatomaceous earth known as CELATOM™ MN-51 was reduced in size to less than 10 micrometers for quantitative X-ray analysis by grinding under ethanol in a vibratory McCrone Micronising Mill for seven minutes. Step-scan X-ray powder-diffraction data were collected over a range 3-80°2θ with CoKa radiation on a Bruker D8 Focus Bragg-Brentano diffractometer equipped with an Fe monochromator foil, 0.6 mm (0.3°) divergence slit, incident- and diffracted-beam Soller slits, and a LynxEye detector. The long fine-focus Co X-ray tube was operated at 35 kV and 40 mA, using a take-off angle of 6°.

Figure 6:
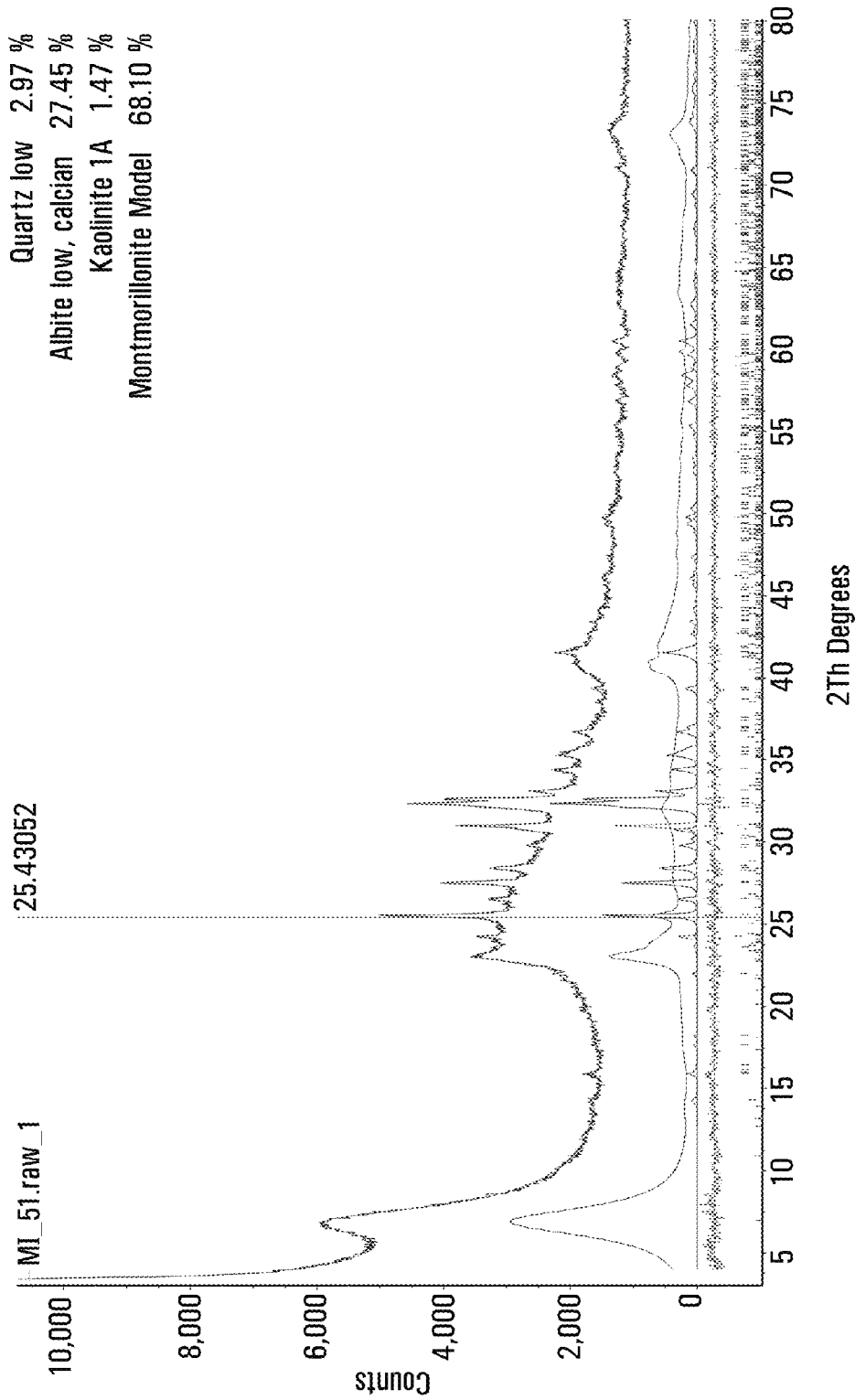
FIG. 6 is a Rietveld refinement plot of the diatomaceous earth known as CELATOM™ MN-51.

The X-ray diffractograms were analyzed using the International Centre for Diffraction Database PDF-4 and Search-Match software by Siemens (Bruker). X-ray powder-diffraction data of the sample were refined with Rietveld program Topas 4.2 (Bruker AXS). FIG. 6 is a Rietveld refinement plot of the diatomaceous earth known as CELATOM™ MN-51. FIG. 6 shows observed intensity at each step and a calculated pattern, and the line below the graph shows the difference between the observed and calculated intensities. The other lines in the graph show individual diffraction patterns of all phases, and the vertical bars represent positions of all Bragg reflections. The amounts given on FIG. 6 are renormalized amorphous-free. The sample contained abundant montmorillonite, which exhibits stacking disorder, so the crystal structure is not predictable. An empirical model was used to account for this phase. In addition, the contribution of amorphous silica was modeled with a peak phase and its amount estimated. The results may be considered semi-quantitative and are in Table 2 below.

TABLE 2

Results of phase analysis of CELATOM ™ MN-51 by Rietveld refinements.

| Mineral | Ideal Formula | Percent by Weight |
|---|---|---|
| Quartz | $\alpha$-$SiO_2$ | 2 |
| Plagioclase | $NaAlSi_3O_8$—$CaAl_2Si_2O_8$ | 18 |
| Kaolinite | $Al_2Si_2O_5(OH)_4$ | 1 |
| Montmorillonite | $(Na,Ca)_{0.3}(Al,Mg)_2Si_4O_{10}(OH)_2 \cdot nH_2O$ | 46 |
| Amorphous Silica | $SiO_2 \cdot nH_2O$ | 33 |

Figure 7:
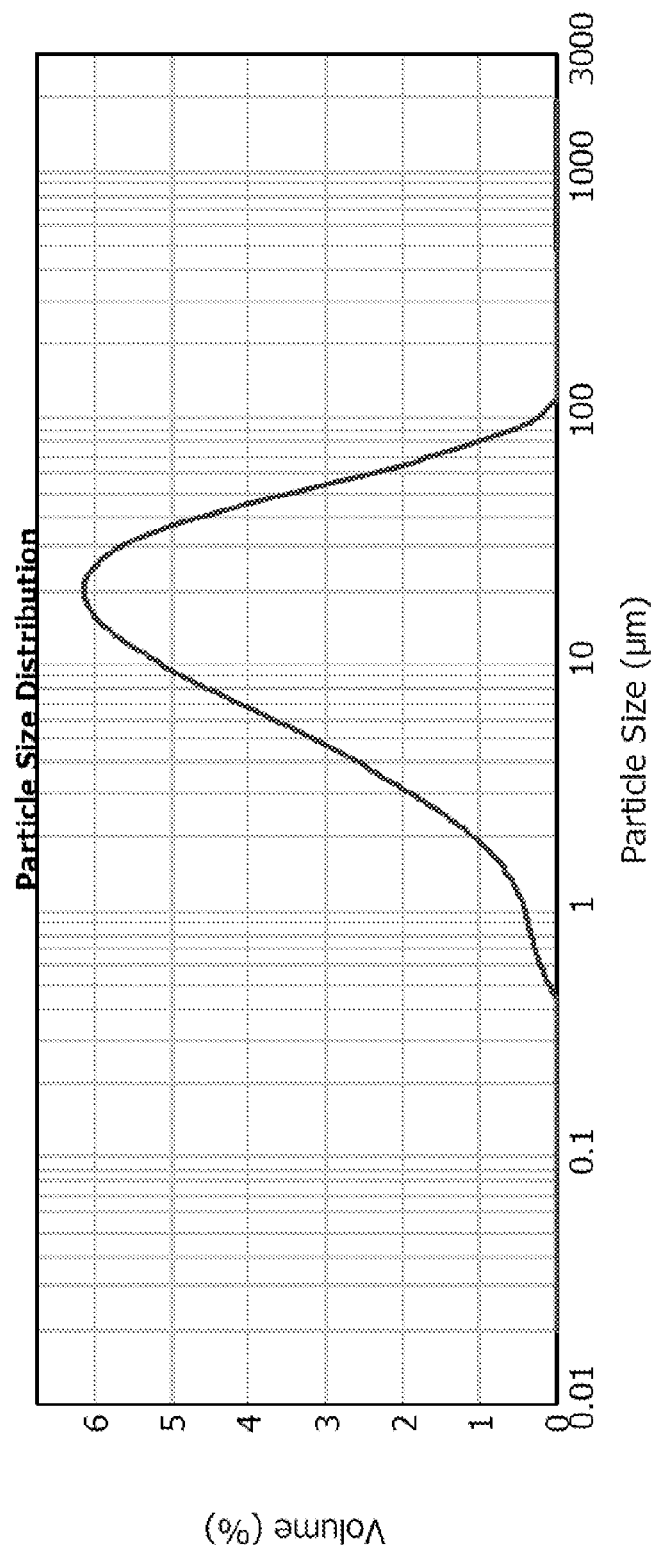
FIG. 7 is a graph of particle size distribution of the diatomaceous earth known as CELATOM™ MN-51.

Particle sizes of sample of the diatomaceous earth known as CELATOM™ MN-51 were measured in a Mastersizer™ 2000 in a water dispersant, and FIG. 7 is a graph of particle size distribution of the diatomaceous earth known as CELATOM™ MN-51.

2. CELATOM™ MN-53

Figure 8:
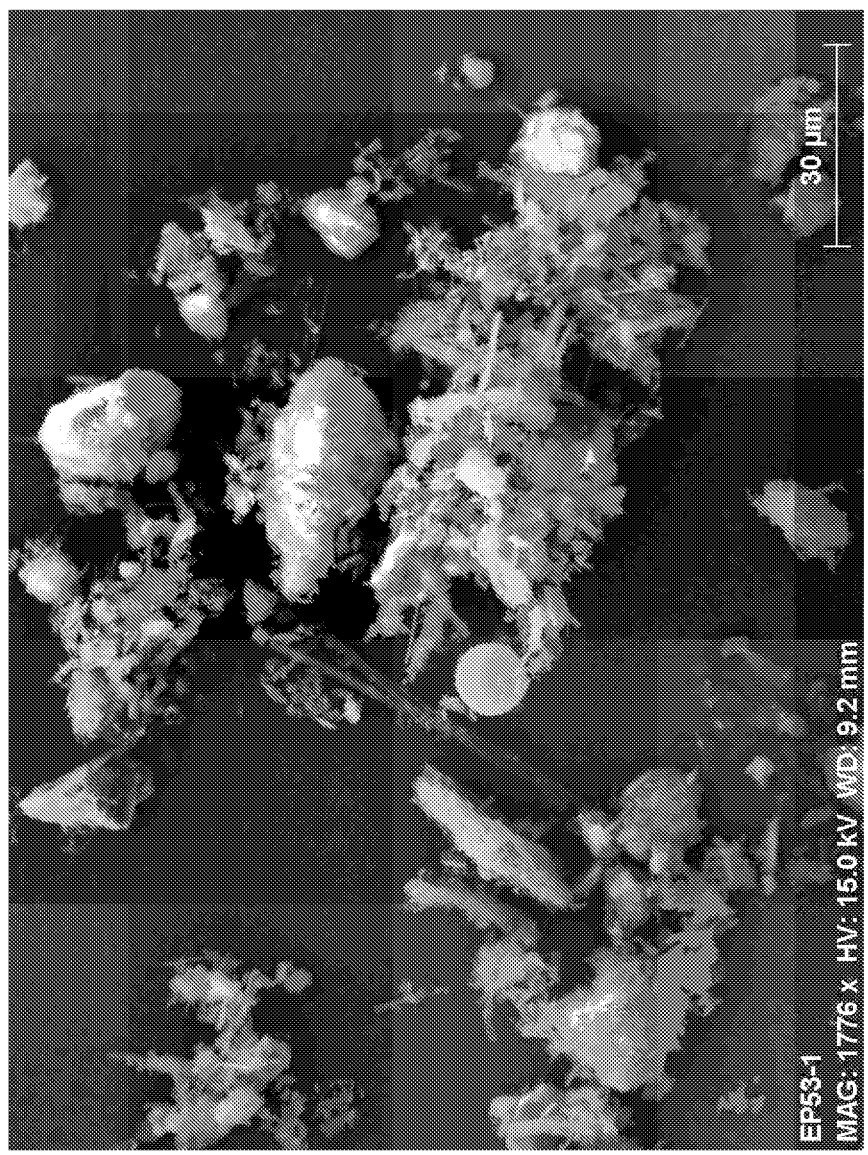
FIG. 8 is a secondary electron image of diatomaceous earth known as CELATOM™ MN-53.

In an alternative embodiment, the diatomaceous earth may include diatomaceous earth known as CELATOM™ MN-53, which is also available from EP Minerals, LLC of 9785 Gateway Drive, Suite 1000, Reno, Nev., United States of America. FIG. 8 is a secondary electron image (using a Philips XL-30 scanning electron microscope after coating with evaporated gold) of the diatomaceous earth known as CELATOM™ MN-53. The diatomaceous earth known as CELATOM™ MN-53 is believed to have the properties given in Table 3 below.

TABLE 3

Properties of CELATOM ™ MN-53.

| Structure | Natural | |
|---|---|---|
| Color | Beige | |
| G.E. Brightness | 65 | |
| Sieve Analysis (Tyler) | 5.0 | |
| % + 325 Mesh (>44 microns) | | |
| Median Particle Diameter (microns) | 14.0 | |
| pH (10% slurry) | 7.0 | |
| Free Moisture | | |
| (Maximum % $H_2O$) | Less than 5.0 | |
| (Typical % $H_2O$) | 3.0 | |

| Density | (lb/ft³) | (g/l) |
|---|---|---|
| Wet Bulk | 31 | 500 |
| Dry Bulk | 11 | 175 |
| Specific Gravity | 2.00 | |
| Refractive Index | 1.46 | |
| Oil Absorption (ASTM F 726-81) % by weight | 150 | |
| Water Absorption (ASTM F 726-81) % by weight | 165 | |
| Chemical Analysis | | |
| $SiO_2$ | 83.7% | |
| $Al_2O_3$ | 5.6% | |
| $Fe_2O_3$ | 2.3% | |
| CaO | 0.9% | |
| MgO | 0.3% | |
| Other Oxides | 1.9% | |
| Loss on Ignition | 5.0% | |

Figure 9:
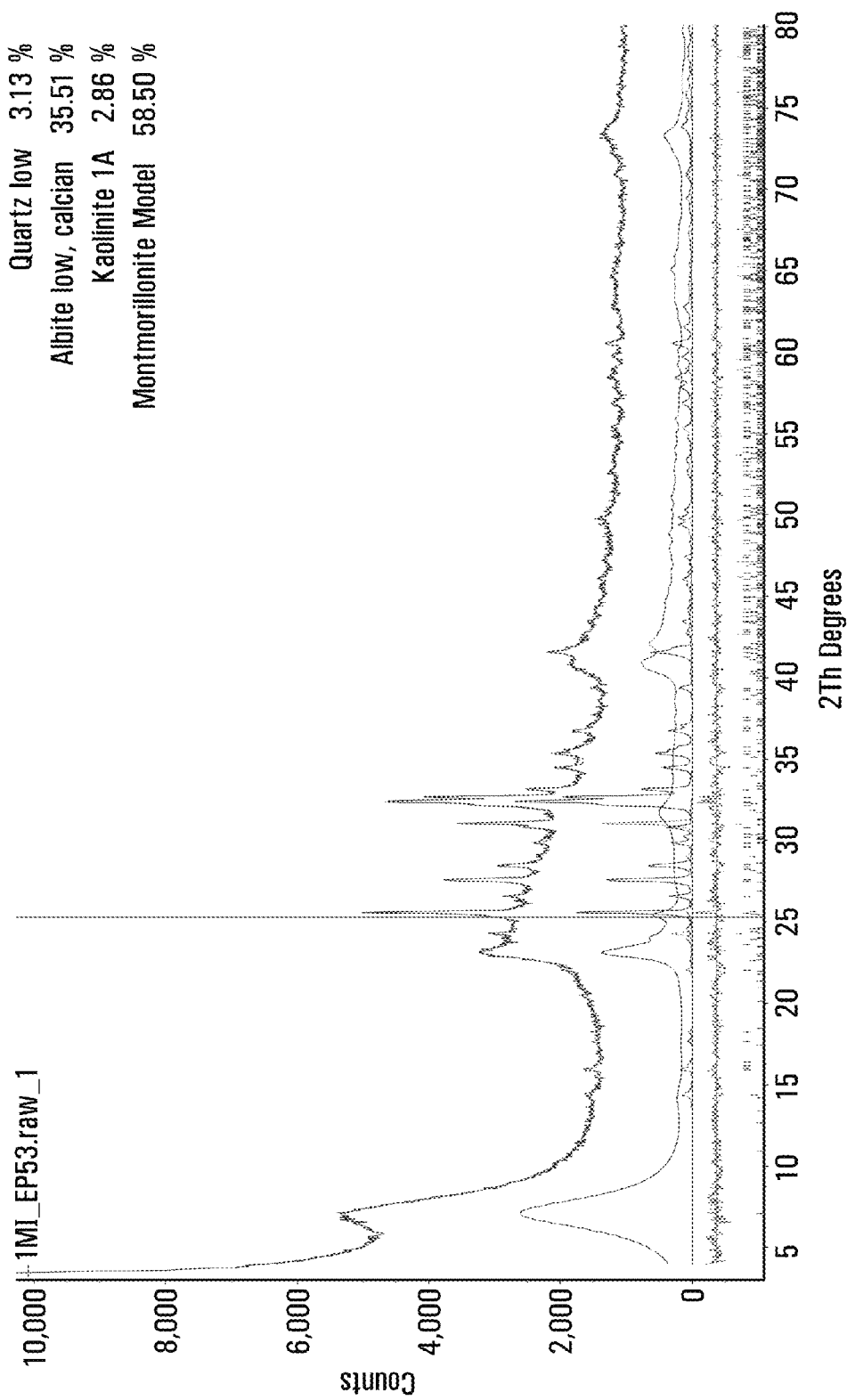
FIG. 9 is a Rietveld refinement plot of the diatomaceous earth known as CELATOM™ MN-53.

FIG. 9 is a Rietveld refinement plot of the diatomaceous earth known as CELATOM™ MN-53 obtained as described above for FIG. 6. FIG. 9 shows observed intensity at each step and a calculated pattern, and the line below the graph shows the difference between the observed and calculated intensities. The other lines in the graph show individual diffraction patterns of all phases, and the vertical bars represent positions of all Bragg reflections. The amounts given on FIG. 9 are renormalized amorphous-free. The results of phase analysis of CELATOM™ MN-53 by Rietveld refinements are in Table 4 below.

TABLE 4

Results of phase analysis of CELATOM ™ MN-53 by Rietveld refinements.

| Mineral | Ideal Formula | Percent by Weight |
|---|---|---|
| Quartz | $\alpha$-$SiO_2$ | 2 |
| Plagioclase | $NaAlSi_3O_8$—$CaAl_2Si_2O_8$ | 24 |
| Kaolinite | $Al_2Si_2O_5(OH)_4$ | 2 |
| Montmorillonite | $(Na,Ca)_{0.3}(Al,Mg)_2Si_4O_{10}(OH)_2 \cdot nH_2O$ | 40 |
| Amorphous Silica | $SiO_2 \cdot nH_2O$ | 31 |

3. Alpine™ Dust

Figure 10:
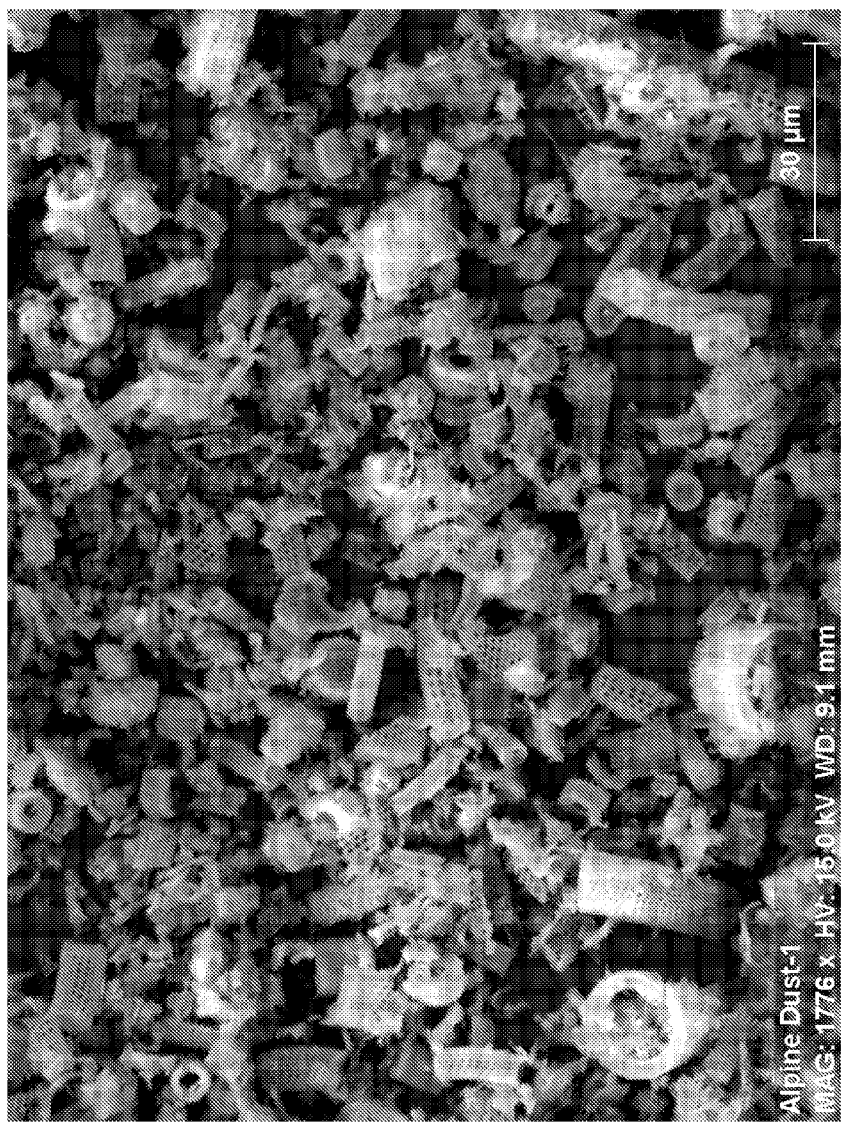
FIG. 10 is a secondary electron image of diatomaceous earth known as Alpine™ Dust.
Figure 11:
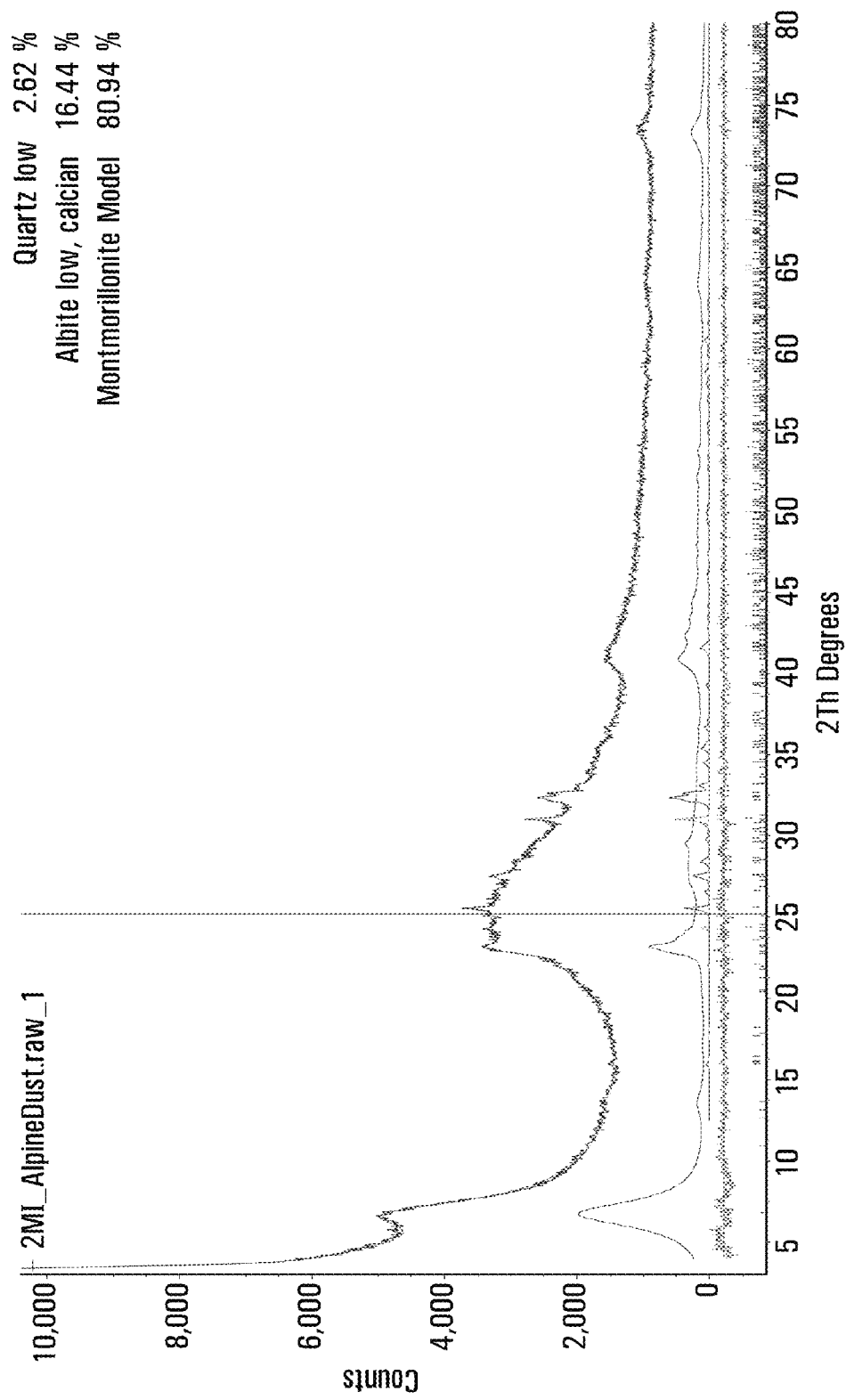
FIG. 11 is a Rietveld refinement plot of the diatomaceous earth known as Alpine™ Dust.

FIG. 10 is a secondary electron image (using a Philips XL-30 scanning electron microscope after coating with evaporated gold) of diatomaceous earth known as Alpine™ Dust ("Prescription Treatment Brand") obtained from Whitmire Micro-Gen Research Laboratories, Inc. of St. Louis, Mo., United States of America, and FIG. 11 is a Rietveld refinement plot of the diatomaceous earth known as Alpine™ Dust obtained as described above for FIG. 6. FIG. 11 shows observed intensity at each step and a calculated pattern, and the line below the graph shows the difference between the observed and calculated intensities. The other lines in the graph show individual diffraction patterns of all phases, and the vertical bars represent positions of all Bragg reflections. The amounts given on FIG. 11 are renormalized amorphous-free. The results of phase analysis of Alpine™ Dust by Rietveld refinements are in Table 5 below.

TABLE 5

Results of phase analysis of Alpine ™ Dust by Rietveld refinements.

| Mineral | Ideal Formula | Percent by Weight |
| --- | --- | --- |
| Quartz | $\alpha$-$SiO_2$ | 1 |
| Plagioclase | $NaAlSi_3O_8$—$CaAl_2Si_2O_8$ | 8 |
| Montmorillonite | $(Na,Ca)_{0.3}(Al,Mg)_2Si_4O_{10}(OH)_2 \cdot nH_2O$ | 38 |
| Amorphous Silica | $SiO_2 \cdot nH_2O$ | 53 |

4. MotherEarth™ D

Figure 12:
FIG. 12 is a secondary electron image of diatomaceous earth known as MotherEarth™ D.
Figure 13:
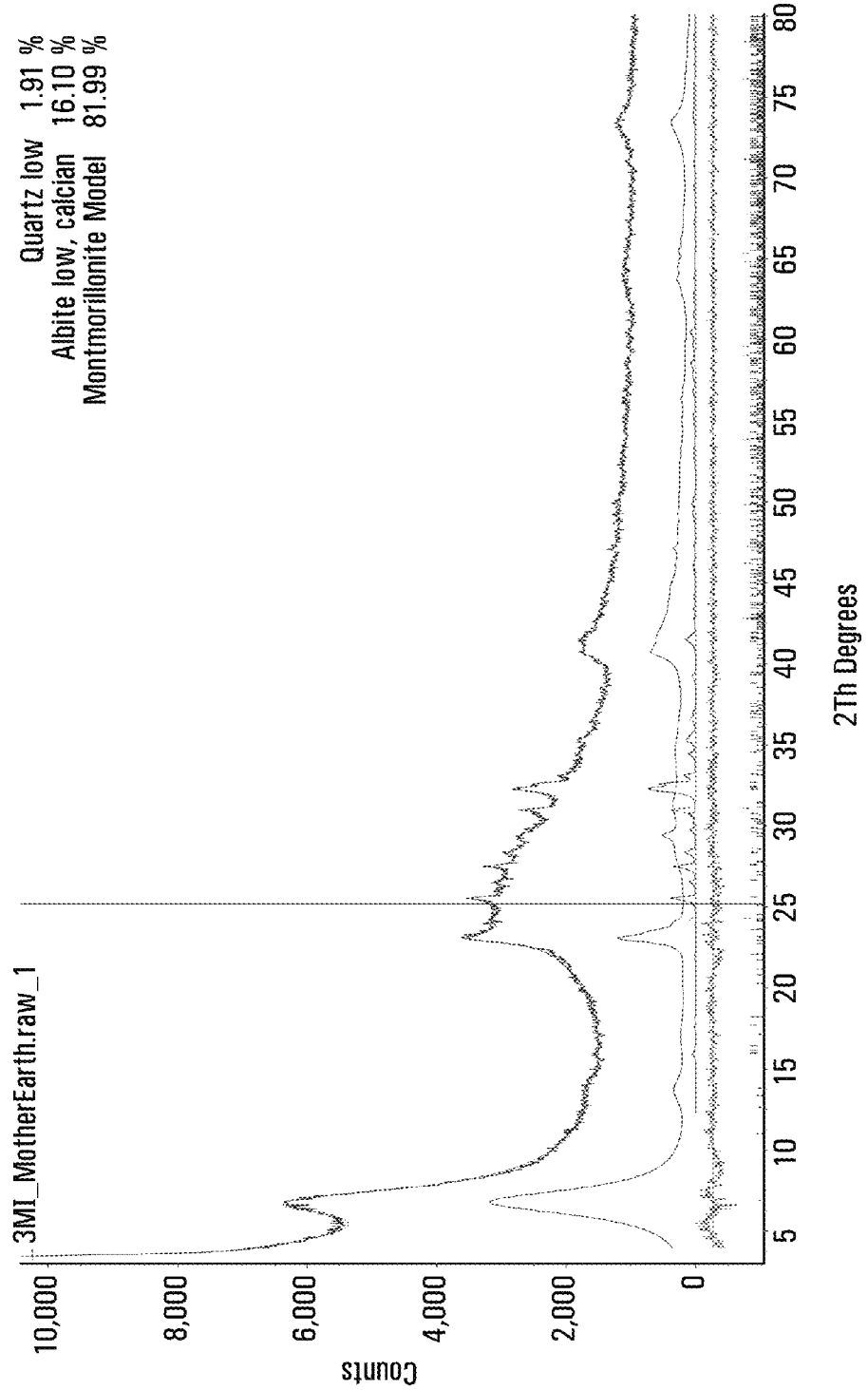
FIG. 13 is a Rietveld refinement plot of the diatomaceous earth known as MotherEarth™ D.

FIG. 12 is a secondary electron image (using a Philips XL-30 scanning electron microscope after coating with evaporated gold) of diatomaceous earth known as MotherEarth™ D obtained from Whitmire Micro-Gen Research Laboratories, Inc. of St. Louis, Mo., United States of America, and FIG. 13 is a Rietveld refinement plot of the diatomaceous earth known as MotherEarth™ D obtained as described above for FIG. 6. FIG. 13 shows observed intensity at each step and a calculated pattern, and the line below the graph shows the difference between the observed and calculated intensities. The other lines in the graph show individual diffraction patterns of all phases, and the vertical bars represent positions of all Bragg reflections. The amounts given on FIG. 13 are renormalized amorphous-free. The results of phase analysis of MotherEarth™ D by Rietveld refinements are in Table 6 below.

TABLE 6

Results of phase analysis of MotherEarth ™ D by Rietveld refinements.

| Mineral | Ideal Formula | Percent by Weight |
| --- | --- | --- |
| Quartz | $\alpha$-$SiO_2$ | 1 |
| Plagioclase | $NaAlSi_3O_8$—$CaAl_2Si_2O_8$ | 9 |
| Montmorillonite | $(Na,Ca)_{0.3}(Al,Mg)_2Si_4O_{10}(OH)_2 \cdot nH_2O$ | 47 |
| Amorphous Silica | $SiO_2 \cdot nH_2O$ | 43 |

Figure 14:
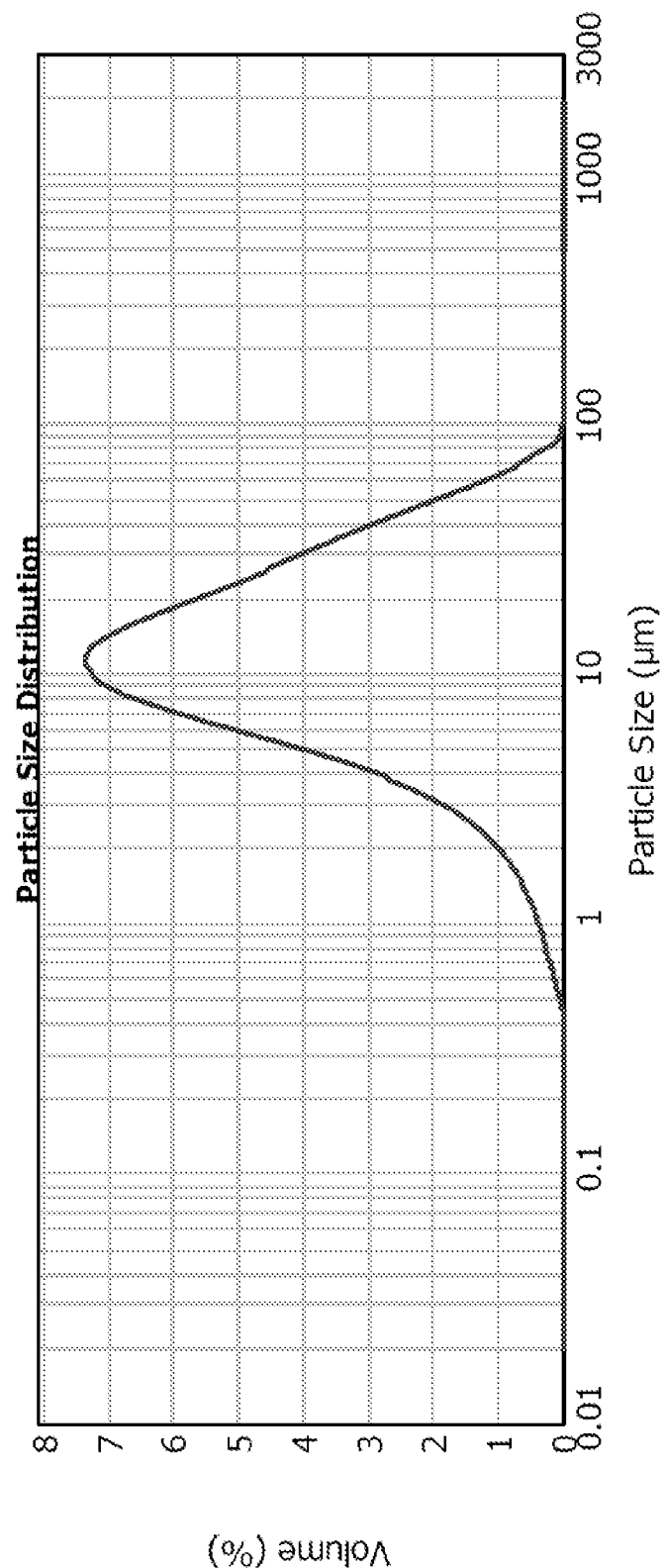
FIG. 14 is a graph of particle size distribution of the diatomaceous earth known as MotherEarth™ D.

Particle sizes of sample of the diatomaceous earth known as MotherEarth™ D were measured in a Mastersizer™ 2000 in a water dispersant, and FIG. 14 is a graph of particle size distribution of the diatomaceous earth known as MotherEarth™ D.

5. PRO-ACTIVE™

Figure 15:
FIGS. 15 to 17 are secondary electron images of diatomaceous earth known as PRO-ACTIVE™.
Figure 16:
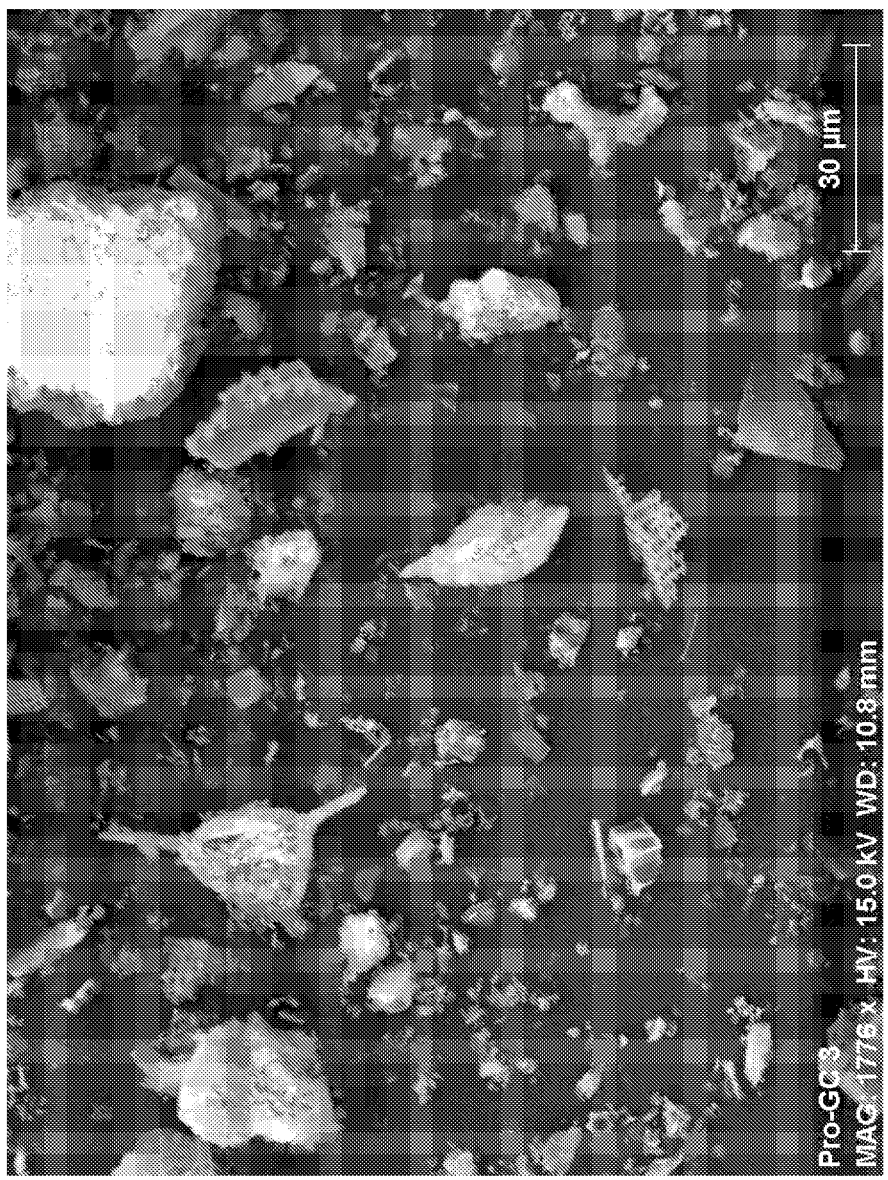
Figure 17:
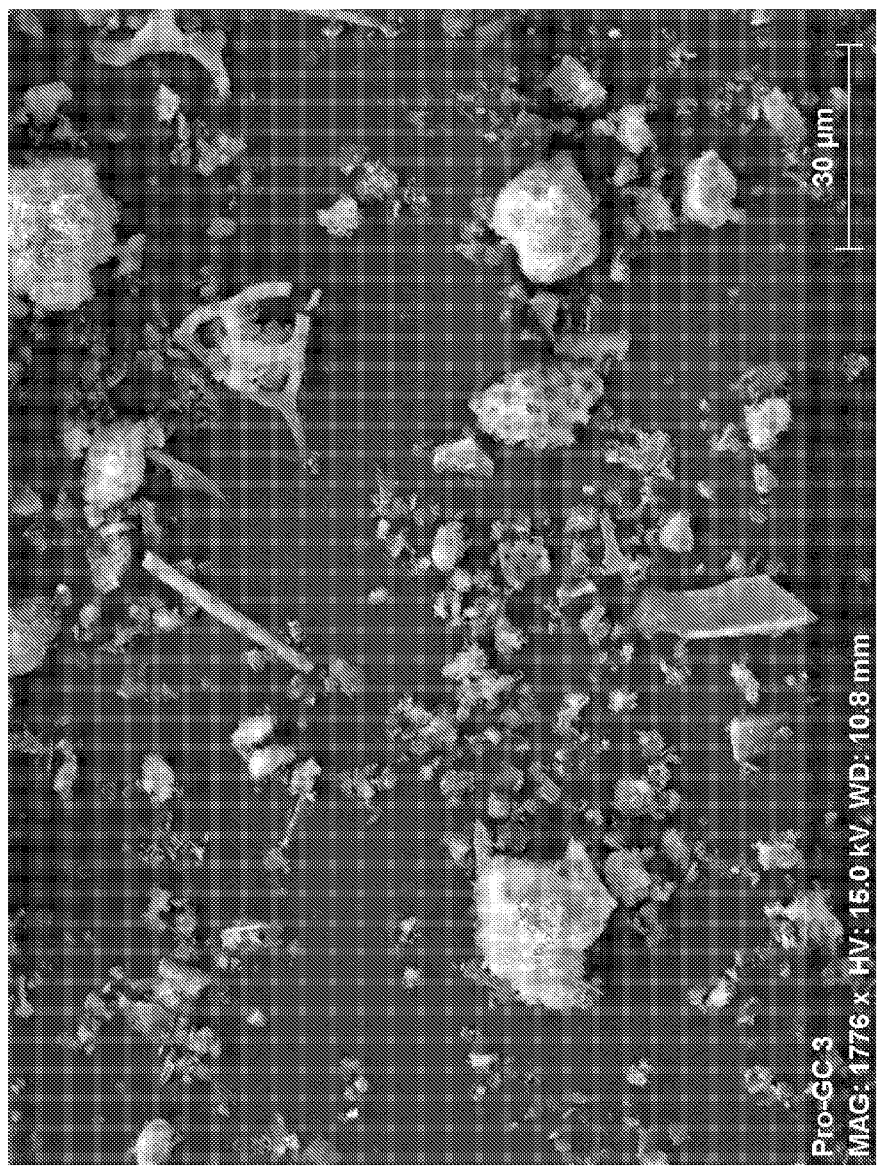
Figure 18:
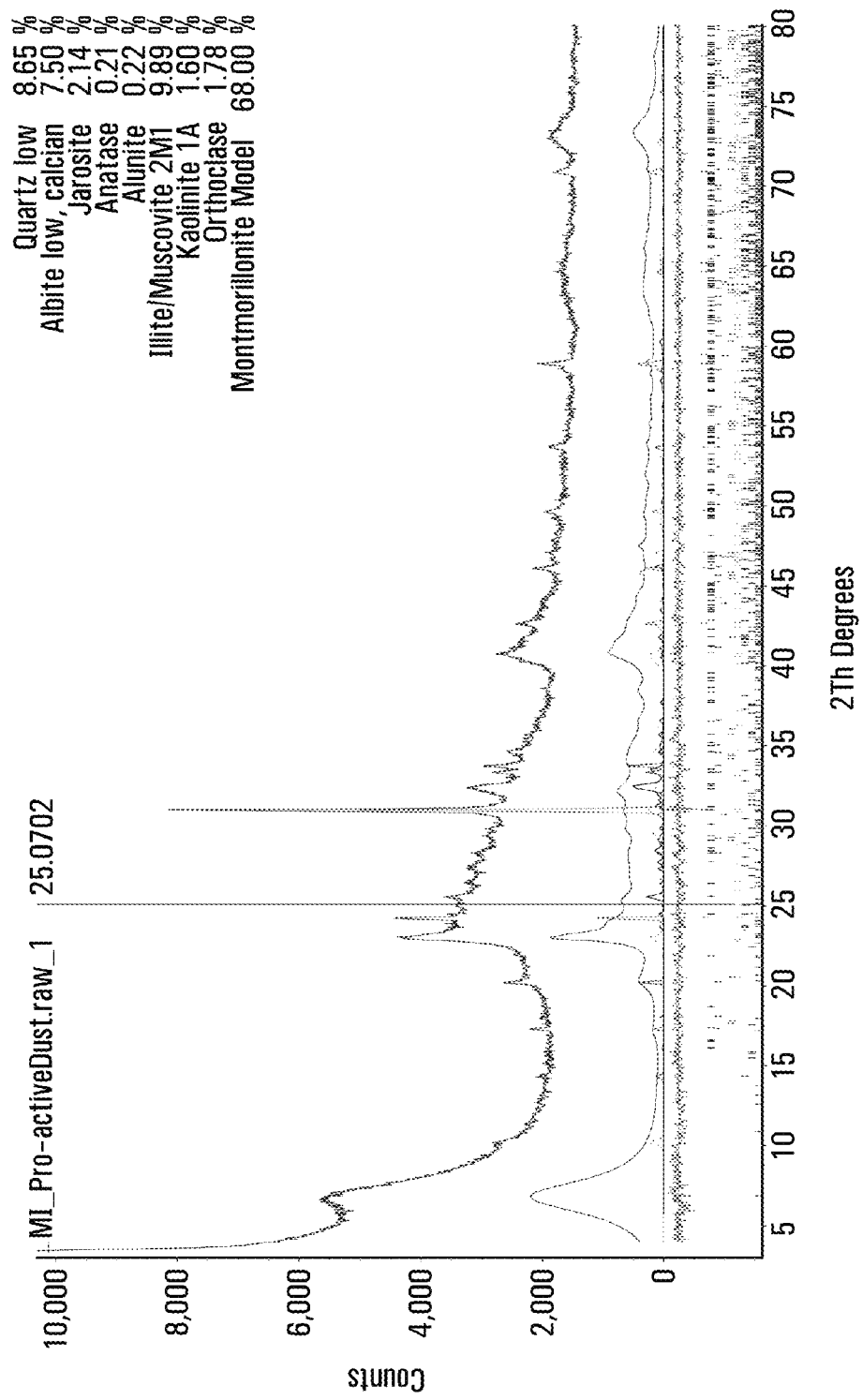
FIG. 18 is a Rietveld refinement plot of the diatomaceous earth known as PRO-ACTIVE™.

FIGS. 15 to 17 are secondary electron images (using a Philips XL-30 scanning electron microscope after coating with evaporated gold) of diatomaceous earth known as PRO-ACTIVE™ obtained from Pest Control Direct Ltd., Hailsham, East Sussex, United Kingdom, and FIG. 18 is a Rietveld refinement plot of the diatomaceous earth known as PRO-ACTIVE™ obtained as described above for FIG. 6. FIG. 18 shows observed intensity at each step and a calculated pattern, and the line below the graph shows the difference between the observed and calculated intensities. The other lines in the graph show individual diffraction patterns of all phases, and the vertical bars represent positions of all Bragg reflections. The amounts given on FIG. 18 are renormalized amorphous-free. The results of phase analysis of PRO-ACTIVE™ by Rietveld refinements are in Table 7 below.

TABLE 7

Results of phase analysis of PRO-ACTIVE ™ by Rietveld refinements.

| Mineral | Ideal Formula | Percent by Weight |
| --- | --- | --- |
| Quartz | $\alpha$-$SiO_2$ | 6 |
| Plagioclase | $NaAlSi_3O_8$—$CaAl_2Si_2O_8$ | 5 |
| Alunite | $K_2Al_6(SO_4)_4(OH)_{12}$ | <1 |
| Jarosite | $K_2Fe_6^{3+}(SO_4)_4(OH)_{12}$ | 2 |
| Anatase | $TiO_2$ | <1 |
| K-feldspar | $KAlSi_3O_8$ | 1 |
| Illite/Muscovite | $K_{0.65}Al_{2.0}Al_{0.65}Si_{3.35}O_{10}(OH)_2$ | 7 |
| Kaolinite | $Al_2Si_2O_5(OH)_4$ | 1 |
| Montmorillonite | $(Na,Ca)_{0.3}(Al,Mg)_2Si_4O_{10}(OH)_2 \cdot nH_2O$ | 50 |
| Amorphous Silica | $SiO_2 \cdot nH_2O$ | 27 |

C. Experiments

Experiment #1

In one experiment ("Experiment #1"), small plastic Petri dishes available from Gelman Sciences™, each about 5.0 cm or about 2.0 inches in diameter, were used in bioassays. A small opening of about 1.5 cm (or about 0.6 inches) in diameter was cut in the lid and closed with a piece of gauze to allow air for bedbug breathing. The Petri dishes were lined with a filter paper about 4.25 cm (or about 1.7 inches) in diameter. Diatomaceous earth was weighed and spread uniformly over the filter paper with forceps. Ten adult field-collected common bedbugs (Cimex lectularius) were introduced in each of the Petri dishes, and the lids were placed over them to prevent their escape. Petri dishes were transferred in a plastic box lined with paper towels sprayed with water to maintain humidity in the box. Experiments were conducted at room temperature, and mortality was noted 24, 48, 72, and 96 hours after the bedbugs were introduced into of the Petri dishes. Four concentrations, between about 0.5 milligrams ("mg") and about 2.0 mg, were used to calculate a lowest lethal concentration sufficient to kill 50% of the bedbugs ("$LC_{50}$") of each product. There was a single replication of 10 bedbugs each.

Tables 8 and 9 below show mortality data from Experiment #1, where "L" refers to a number of bedbugs still living after a corresponding time given in the tables, and where "D" refers to a number that died after the time given.

TABLE 8

Toxicity of adult bedbugs to CELATOM ™ MN-51.

| | Amount of CELATOM ™ MN-51 | | | | | | |
| --- | --- | --- | --- | --- | --- | --- | --- |
| Time | 2.0 mg | | 1.0 mg | | 0.8 mg | | 0.5 mg |
| (hours) | L | D | L | D | L | D | L | D |
| 48 | 0 | 10 | 3 | 7 | 4 | 6 | 5 | 5 |
| 72 | | 0 | | 3 | 0 | 4 | 0 | 5 |

TABLE 9

Toxicity of adult bedbugs to CELATOM ™ MN-53.

| Time | Amount of CELATOM ™ MN-53 | | | | | | | |
|---|---|---|---|---|---|---|---|---|
| | 2.0 mg | | 1.0 mg | | 0.8 mg | | 0.5 mg | |
| (hours) | L | D | L | D | L | D | L | D |
| 48 | 6 | 4 | 9 | 1 | 7 | 3 | 8 | 2 |
| 72 | 6 | 4 | 9 | 1 | 7 | 3 | 8 | 2 |
| 96 | 0 | 10 | 4 | 6 | 6 | 4 | 7 | 3 |

All of the bedbugs died in CELATOM™ MN-51 diatomaceous earth after 48 hours. Therefore, $LC_{50}$ for CELATOM™ MN-51 was calculated for 48 hours only, and $LC_{50}$ after 48 hours for CELATOM™ MN-51 was calculated as 0.7 mg. The data after 48 hours for CELATOM™ MN-53 were not good for calculation, and therefore $LC_{50}$ for CELATOM™ MN-53 was calculated after 96 hours as 0.8 mg (0.552-1.052).

Experiment #2

In another experiment ("Experiment #2"), mortality of CELATOM™ MN-51 was compared with the diatomaceous earth products known as Alpine™ Dust, MotherEarth™ D, and PRO-ACTIVE™. The various products were applied with forceps and weighed on a small filter paper, which was then placed in a Petri dish (about 5.0 cm or about 2 inches diameter). Common bedbugs (*Cimex lectularius*) were introduced in the various Petri dishes, and mortality was assessed in each of the Petri dishes after 24 hours and after 48 hours. Four to five concentrations of each product were used, the concentrations ranging from 0.25 mg to 6 mg, and there were three replications of between 9 and 11 bedbugs (adults or last instar nymphs) in each replication. A probit analysis was used to calculate $LC_{50}$ and $LC_{95}$ (lowest lethal concentrations sufficient to kill 95% of the bedbugs) values and 95% confidence intervals ("CIs") for the $LC_{50}$ and $LC_{95}$ values, as shown in Table 10 below.

TABLE 10

$LC_{50}$, $LC_{95}$, and CI for CELATOM ™ MN-51, Alpine ™ Dust, and MotherEarth ™ D.

| Product | Time (hours) | $LC_{50}$ (mg) | CI of $LC_{50}$ (mg) | $LC_{95}$ (mg) | CI of $LC_{95}$ (mg) |
|---|---|---|---|---|---|
| CELATOM ™ MN-51 | 24 | 0.24 | 0.1-0.32 | 0.95 | 0.69-1.98 |
| Alpine ™ Dust | 24 | 6.36 | 3.83-29.27 | 52.57 | 15.88-3366 |
| Alpine ™ Dust | 48 | 1.72 | 1.37-2.18 | 6.6 | 4.47-13.44 |
| MotherEarth ™ D | 24 | 0.26 | 0.14-0.36 | 1.37 | 0.91-3.44 |
| PRO-ACTIVE ™ | 24 | 3.2 | 2.28-5.34 | 28.8 | 12.8-192.4 |

Experiment #3

In another experiment ("Experiment #3"), six Petri dishes (each about 5.0 cm or about 2.0 inches in diameter) were sprayed with an aerosol including CELATOM™ MN-51 using an apparatus similar to the spray apparatus 100 shown in FIG. 1, and a thin coating of the CELATOM™ MN-51 remained after drying; those six Petri dishes were used for an experimental group. An additional six Petri dishes (each 5.0 cm or about 2.0 inches in diameter) did not receive the aerosol or the diatomaceous earth; those six Petri dishes were used for a control group. Five adult common bedbugs (*Cimex lectularius*) were introduced with forceps into each of the 12 Petri dishes, and lids were applied to prevent the bedbugs from escaping. Mortality was assessed 3, 15, 18, and 24 hours after the bedbugs were introduced into the Petri dishes, and there was no mortality in the control group. Mortality in the experimental group is shown in Table 11 below.

TABLE 11

Number of bedbugs dead from aerosol including CELATOM ™ MN-51.

| Petri dish number | Number dead after 3 hours | Number dead after 15 hours | Number dead after 18 hours | Number dead after 24 hours |
|---|---|---|---|---|
| 1 | 0 | 5 | 5 | 5 |
| 2 | 0 | 2 | 3 | 5 |
| 3 | 0 | 5 | 5 | 5 |
| 4 | 0 | 4 | 5 | 5 |
| 5 | 0 | 5 | 5 | 5 |
| 6 | 0 | 3 | 3 | 5 |
| Total | 0 | 24 | 26 | 30 |

Thus, in Experiment #3, all of the bedbugs exposed to the aerosol including CELATOM™ MN-51 died within 24 hours, whereas none of the control group bedbugs died within 24 hours.

Experiment #4

Another experiment ("Experiment #4") involved plastic RUBBERMAID™ translucent boxes (about 73.6 cm×about 45.7 cm×about 33.7 cm, or about 29 inches×about 18 inches×about 13.3 inches), more particularly two such boxes as experimental boxes and two such boxes as control boxes. A section about 20 cm (or about 7.9 inches) wide in the center of each of the experimental boxes was sprayed with the aerosol including CELATOM™ MN-51 and allowed to dry. A piece of a field-collected sheet (about 50 cm×about 24 cm, or about 19.7 inches×about 7.9 inches) was lined on one side of each of the boxes and used as a stimulant. The sheet was collected from a home infested with bedbugs, and had eggs and many freshly fed bedbugs, but the bedbugs were collected from the sheet before placing pieces of the sheet into the boxes. Sides of the boxes opposite the pieces of the field-collected sheet were lined with a clean and new piece of cloth. Fifty adult common bedbugs (*Cimex lectularius*) were introduced into each box on the clean cloth, and then the box was closed with a lid. The control boxes were similar to the experimental boxes but did not include the aerosol.

In all four of the boxes, the bedbugs moved from the sides of the boxes having the clean cloths to the sides of the boxes having the pieces of the field-collected sheet. There was no mortality in the control boxes after 48 hours, but after 24 hours, one of the experimental boxes had mortality of 43 of the 50 bedbugs, and the other of the experimental boxes had mortality of 45 of the 50 bedbugs. All of the bedbugs in the experimental boxes died after 48 hours. The bedbugs were found dead lying on their backs and dusted with the product from the aerosol.

Experiment #5

Another experiment ("Experiment #5") was the same as Experiment #4 except that 100 common bedbugs (*Cimex lectularius*) were introduced on the clean piece of cloth as described for Experiment #4. Insects again moved from one side of the box to the other in all cases. There was no mortality in the control boxes, whereas after 18 hours, 99 bedbugs died in one of the experimental boxes and 98 bedbugs died in the other one of the experimental boxes. All of the bedbugs in both experimental boxes died after 24 hours.

Experiment #6

In one experiment (Experiment #6), 1.5 mg of diatomaceous earth was placed on a piece of filter paper. One adult common bedbug (*Cimex lectularius*) (the "treaded bedbug") was dusted by introducing it on the filter paper using forceps. The treated bedbug was then introduced in a Petri dish (about 5.0 cm or about 2.0 inches in diameter) containing 4 untreated adult common bedbugs (*Cimex lectularius*). Both CELATOM™ MN-51 and MotherEarth™ D diatomaceous earths were tested using this method. Control Petri dishes contained five bedbugs, none of which was dusted with diatomaceous earth. There were six replications with five bedbugs in each. Petri dishes were placed in a plastic box with a lid, and mortality was assessed after 24 hours, 48 hours, and 96 hours. Table 12 below shows the number of bedbugs dead in each of the six replications for CELATOM™ MN-51, MotherEarth™ D, and control Petri dishes after 24 hours, 48 hours, and 96 hours.

TABLE 12

Number of bedbugs dead for CELATOM ™ MN-51 ("51"), MotherEarth ™ D ("ME"), and control ("C") Petri dishes.

| Petri Dish | Number Dead After 24 Hours | | | Number Dead After 48 Hours | | | Number Dead After 96 Hours | | |
|---|---|---|---|---|---|---|---|---|---|
| | 51 | ME | C | 51 | ME | C | 51 | ME | C |
| 1 | 0 | 0 | 0 | 0 | 0 | 0 | 2 | 3 | 2 |
| 2 | 0 | 0 | 0 | 0 | 0 | 0 | 5 | 1 | 3 |
| 3 | 0 | 0 | 0 | 0 | 0 | 0 | 4 | 5 | 1 |
| 4 | 0 | 0 | 0 | 0 | 0 | 0 | 4 | 4 | 1 |
| 5 | 0 | 0 | 0 | 0 | 0 | 0 | 4 | 1 | 1 |
| 6 | 1 | 0 | 0 | 1 | 0 | 0 | 4 | 2 | 0 |
| Total | 1 | 0 | 0 | 1 | 0 | 0 | 23 | 16 | 8 |

Experiment #7

In another experiment (Experiment #7), 2.0 mg of either CELATOM™ MN-51 or MotherEarth™ D diatomaceous earth was mixed with a red fluorescent dust from a luminous powder kit #1162A obtained from BioQuip Products Inc., Rancho Dominguez, Calif., United States of America and placed on a piece of filter paper. One adult common bedbug (*Cimex lectularius*) was dusted by introducing it on the filter paper using forceps. The dusted bedbug was then introduced in a Petri dish (about 5.0 cm or about 2.0 inches in diameter) containing 4 untreated adult common bedbugs (*Cimex lectularius*). All Petri dishes were then placed in a plastic box with a lid. Control Petri dishes contained five adult common bedbugs (*Cimex lectularius*), none of which has been dusted with diatomaceous earth. There were three replications of each condition, and mortality was assessed after 16 hours. The mortality data are shown in Table 13 below.

TABLE 13

Number of bedbugs dead after 16 hours for CELATOM ™ MN-51, MotherEarth ™ D, and control Petri dishes.

| Petri Dish | CELATOM ™ MN-51 | MotherEarth ™ D | Control |
|---|---|---|---|
| 1 | 3 | 1 | 0 |
| 2 | 4 | 3 | 0 |
| 3 | 4 | 2 | 0 |
| Total | 11 (61.1%) | 6 (33.3%) | 0 |

The fluorescent dye was visibly observed on the bedbugs that did not contact the diatomaceous earth directly, suggesting that such bedbugs came into contact with diatomaceous earth by contacting the bedbug that had contacted the diatomaceous earth directly.

Experiment #8

In another experiment ("Experiment #8"), diatomaceous earth dusts were weighed on filter paper (Fisher™ brand, about 5.5 cm or about 2.2 inches in diameter). The filter papers were shaken about 3 or 4 times to remove excess dust and were weighed again to measure diatomaceous earth remaining on the paper. Table 14 below shows the weight of dust before shaking, the weight of dust remaining after shaking, and the amount lost from shaking as the difference between the weight of dust before shaking and the weight of dust after shaking.

TABLE 14

Weights of dust before shaking, after shaking, and amounts lost from shaking.

| Product Applied as Dust | Weight before Shaking (mg) | Weight after Shaking (mg) | Amount Lost from Shaking (mg) |
|---|---|---|---|
| PRO-ACTIVE ™ | 5 | 1.8 | 3.2 |
| | 5.3 | 2.7 | 2.6 |
| | 6 | 3.1 | 2.9 |
| mean | 5.4 | 2.5 | 2.9 |
| Alpine ™ Dust | 6.6 | 3.9 | 2.7 |
| | 5.3 | 3.2 | 2.1 |
| | 5.5 | 3.5 | 2 |
| mean | 5.8 | 3.5 | 2.3 |
| MotherEarth ™ D | 6.5 | 3.4 | 3.1 |
| | 6.5 | 4.3 | 2.2 |
| | 6.8 | 3.7 | 3.1 |
| mean | 6.6 | 3.8 | 2.8 |

Similarly, filter paper was weighed, sprayed with aerosol, dried, and weighed again to measure the diatomaceous earth residue. There were three replications for each diatomaceous earth sample tested. Table 15 below shows weights of filter paper before and after spraying aerosol with diatomaceous earth, and amounts of diatomaceous earth added from spraying.

TABLE 15

Weights of filter paper before and after spraying aerosol, and amounts of diatomaceous earth added from spraying.

| Product Applied in Aerosol Spray | Weight before Spraying (mg) | Weight after Spraying (mg) | Amount Added from Spraying (mg) |
|---|---|---|---|
| CELATOM ™ MN-51 | 164 | 175 | 11 |
| | 157.4 | 173 | 15.6 |
| | 162 | 176 | 14 |
| mean | 161.1 | 174.7 | 13.5 |
| CELATOM ™ MN-51 (in reduced spraying volume) | 151.1 | 152.8 | 1.7 |
| | 169.4 | 175.8 | 6.4 |
| | 162 | 170 | 8 |
| mean | 160.8 | 166.2 | 5.4 |

Experiment #9

In another experiment ("Experiment #9"), a sample of CELATOM™ MN-51 was size-separated to separate into a smaller size fraction of particles less than about 11 micrometers in size and into a larger size fraction of particles larger than about 11 micrometers in size. The CELATOM™ MN-51 sample was size separated in a centrifuge, and because some particles of CELATOM™ MN-51 are non-spherical, 11 micrometers is an approximate separation size and, for example, the smaller size fraction may include elongate particles that are longer than 11 micrometers. In general herein, "a smaller size fraction of particles less than about 11 micrometers in size" may in some embodiments include a smaller size fraction from centrifugal size separation that may include elongate particles that are longer than 11 micrometers.

Figure 19:
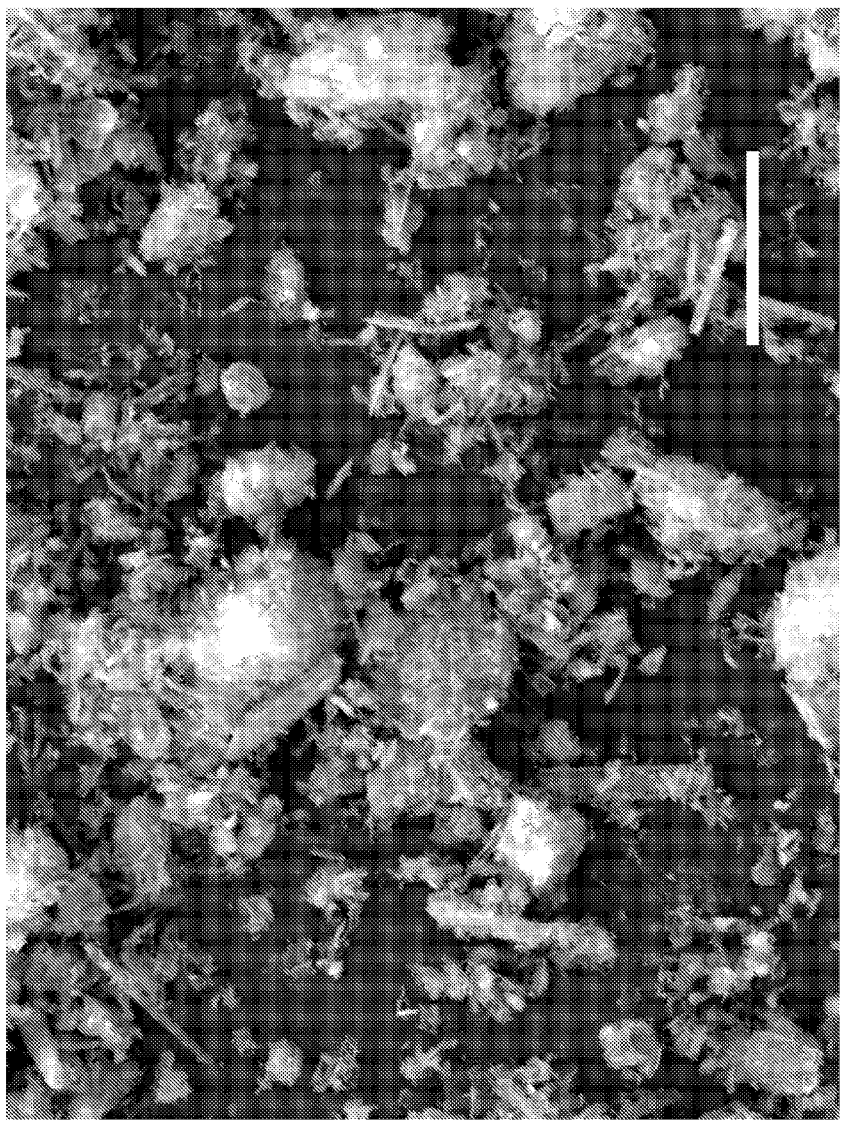
FIG. 19 is a scanning electron microscope image of a smaller size fraction of the diatomaceous earth known as CELATOM™ MN-51.
Figure 20:
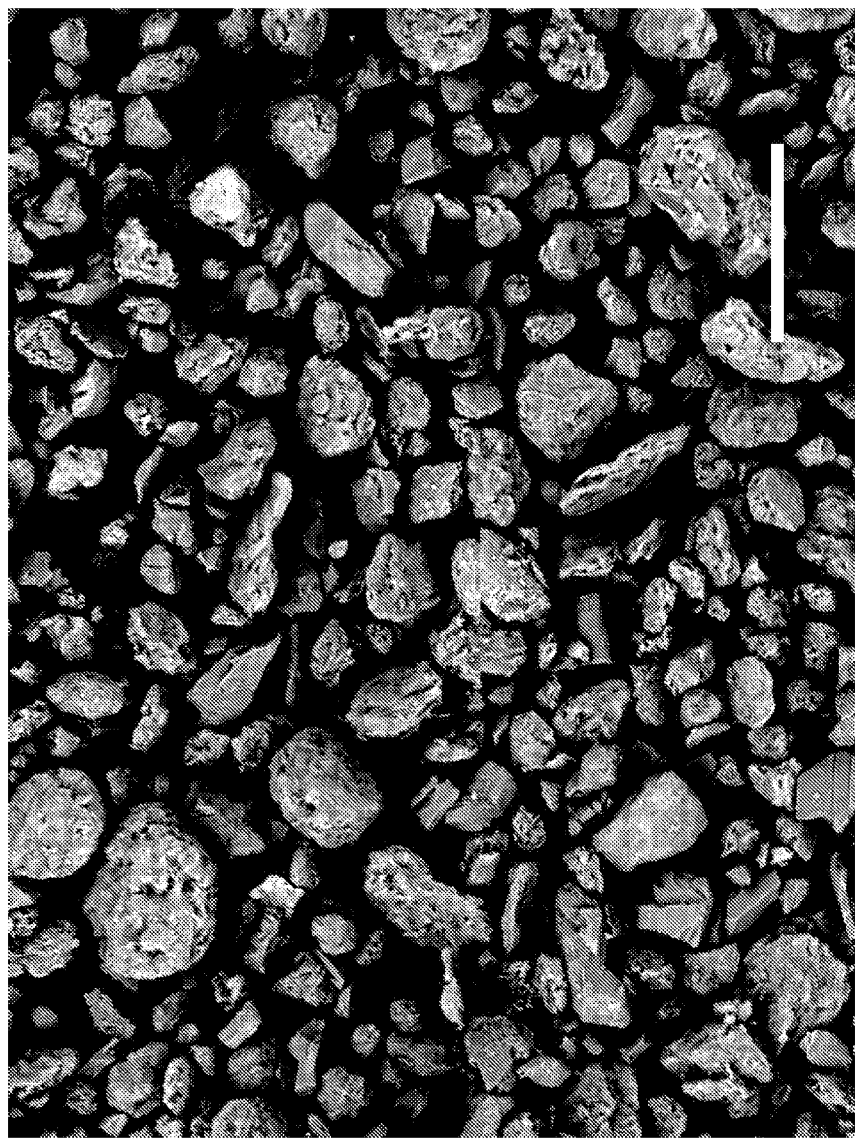
FIG. 20 is a scanning electron microscope image of a larger size fraction of the diatomaceous earth known as CELATOM™ MN-51.

The size-separated powders were examined using a Philips XL-30 scanning electron microscope after coating with evaporated gold. FIG. 19 is a scanning electron microscope image of the smaller size fraction (particles less than about 11 micrometers in size) and FIG. 20 is a scanning electron microscope image of the larger size fraction (particles larger than about 11 micrometers in size). The scale bar in FIG. 19 represents 30 micrometers, whereas the scale bar in FIG. 20 represents 120 micrometers. The original sample of CELATOM™ MN-51 was reduced in weight by about 30% after the larger size fraction (particles larger than about 11 micrometers in size) was removed from it.

Efficacy against bedbugs of the smaller size fraction of CELATOM™ MN-51 and of the larger size fraction of CELATOM™ MN-51 was measured in three replications of eight adult common bedbugs (*Cimex lectularius*) each, for a total of 24 bedbugs introduced. Samples were weighed and spread on filter papers in Petri dishes, and the bedbugs were then introduced. Mortality assessed after 24 hours and after 48 hours. Table 16 below shows the number of the initially introduced 24 bedbugs that were killed after 24 and after 48 hours when exposed to 1, 2, 4, and 8 mg of the smaller size fraction of CELATOM™ MN-51 and of the larger size fraction of CELATOM™ MN-51.

TABLE 16

Recorded mortality for size-separated CELATOM ™ MN-51 and unseparated CELATOM ™ MN-51.

| Amount (mg) | Smaller Size Fraction of CELATOM ™ MN-51 | | Larger Size Fraction of CELATOM ™ MN-51 | |
| --- | --- | --- | --- | --- |
| | Number killed after 24 hours | Number killed after 48 hours | Number killed after 24 hours | Number killed after 48 hours |
| 1 | 8 | 20 | 0 | 0 |
| 2 | 10 | 21 | 1 | 1 |
| 4 | 14 | 22 | 2 | 2 |
| 8 | 15 | 24 | 3 | 3 |

From the data above, $LC_{50}$ may be calculated as shown in Table 17 below. Table 17 also shows confidence intervals of $LC_{50}$ in brackets where the confidence intervals were also calculated.

TABLE 17

$LC_{50}$ for size-separated CELATOM ™ MN-51.

| Sample | $LC_{50}$ after 24 hours (mg) | $LC_{50}$ after 48 hours (mg) |
| --- | --- | --- |
| Smaller Size Fraction of CELATOM ™ MN-51 | 3.038 (0.983-13.803) | 0.201 (0.000-0.688) |
| Larger Size Fraction of CELATOM ™ MN-51 | 50.221 | 50.221 |

D. Discussion of Experiments and of Uses of Diatomaceous Earth

In general, and without wishing to be bound by any theory, it is believed that diatomaceous earth may damage exoskeletons of animals having exoskeletons, which damage may lead to dehydration and death of the animals. Therefore, it is believed that diatomaceous earth, and various apparatuses such as the spray apparatus 100 as described herein for example, may be effective in the control of populations of one or more of animals having exoskeletons, including arthropods, arachnids, insects, and bedbugs. Herein, "bedbugs" may refer to common bedbugs (*Cimex lectularius*), or more generally to *Cimex*, or still more generally to *Cimicidae*, for example. Animal populations that may be controlled by diatomaceous earth in other embodiments may also include cockroaches, ants, fleas, and other pests. Herein, "control" of an animal population may in various embodiments include prevention of growth or survival of such a population before discovery of the population, and also killing one or more members of such a population after discovery of the population.

Also without wishing to be bound by any theory, it is believed that diatomaceous earth may additionally or alternatively block or otherwise interfere with spiracles on exoskeletons of bedbugs, thereby diminishing or eliminating passage of air into the trachea of the bedbugs and potentially asphyxiating the bedbugs.

Experiment #1 appears to indicate that $LC_{50}$ for CELATOM™ MN-51 after 48 hours is less than or comparable to $LC_{50}$ for CELATOM™ MN-53 after 96 hours. In other words, from Experiment #1, CELATOM™ MN-51 appears to kill at least as many bedbugs in 48 hours as CELATOM™ MN-53 kills in 96 hours. Also, Experiment #2 appears to indicate that $LC_{50}$ and $LC_{95}$ after 24 hours for CELATOM™ MN-51 are significantly less than $LC_{50}$ and $LC_{95}$ after 24 hours for Alpine™ Dust and for PRO-ACTIVE™ because the confidence intervals for those $LC_{50}$ and $LC_{95}$ values do not overlap. Moreover, from Experiment #2, CELATOM™ MN-51 appears to kill significantly more bedbugs in 24 hours than Alpine™ Dust kills in 48 hours. Therefore, Experiment #1 and Experiment #2 appear to indicate CELATOM™ MN-51 is more effective at killing bedbugs, and thus in controlling bedbug populations, than CELATOM™ MN-53, Alpine™ Dust, and PRO-ACTIVE™.

Experiment #2 appears to indicate that to $LC_{50}$ and $LC_{95}$ after 24 hours for CELATOM™ MN-51 are less than $LC_{50}$ and $LC_{95}$ after 24 hours for MotherEarth™ D, but the confidence intervals for those $LC_{50}$ and $LC_{95}$ values overlap. Therefore, according to Experiment #2, CELATOM™ MN-51 may be more effective than MotherEarth™ D at killing bedbugs, and thus in controlling bedbug populations, but overlap in the confidence intervals raises some uncertainty. However, Experiment #6 appears to indicate that when one bedbug contacted CELATOM™ MN-51, that one bedbug was generally more effective at killing other bedbugs by transmitting the CELATOM™ MN-51 to the other bedbugs than was the case for MotherEarth™ D. Because bedbugs appear to pick up diatomaceous earth even when briefly exposed to the diatomaceous earth (such as by crossing an area treated with CELATOM™ MN-51 as in Experiment #4 and in Experiment #5), because bedbugs appear to pass diatomaceous earth to other bedbugs (see Experiment #6 and Experiment #7), and because CELATOM™ MN-51 appears to be more effective than MotherEarth™ D in killing bedbugs by transmission of diatomaceous earth from one bedbug to other bedbugs (see Experiment #6), it is believed that overall CELATOM™ MN-51 may be more effective than MotherEarth™ D in controlling bedbug populations.

In view of the foregoing, it is believed that CELATOM™ MN-51 may be more effective in controlling bedbug populations than the other diatomaceous earth products described above.

As indicated above, different insect species have different bodies that may be affected significantly differently by different types of diatomaceous earth. Without wishing to be bound by any theory, it is believed that some characteristics of CELATOM™ MN-51 may increase the effectiveness of CELATOM™ MN-51 when compared to other varieties of diatomaceous earth. For example, some characteristics of CELATOM™ MN-51 may increase the likelihood of diatomaceous earth being transmitted from one bedbug to another, thereby apparently increasing effectiveness of CELATOM™ MN-51 in controlling bedbug populations when compared to MotherEarth™ D as shown in Experiment #6.

In Experiment #9, a sample of CELATOM™ MN-51 was size separated into a smaller size fraction and into a larger size fraction, and Experiment #9 appears to indicate that the smaller size fraction was significantly more effective than the larger size fraction at killing bedbugs. FIG. 17 illustrates fine grained, broken diatom frustules in the smaller size fraction. Larger grains are absent, but there are aggregates of broken diatom frustules of, roughly, tens of micrometers. In contrast, FIG. 20 illustrates grains that range in size from tens of micrometers to approximately 100 micrometers in length in the larger size fraction. Many grains in FIG. 20 appear not to be diatomaceous material, but rather mineral grains. Therefore, Experiment #9 appears to indicate that the diatom frustules of CELATOM™ MN-51 are more effective at killing bedbugs than other components of CELATOM™ MN-51.

As shown in FIGS. 2 to 5, some of the particles of CELATOM™ MN-51 appear to be remains of diatoms having frustules having widths less than about 3 micrometers or less than about 5 micrometers and lengths greater than about 20 micrometers or greater than about 30 micrometers. It is believed that such diatoms may be *Fragilaria, Tabularia,* or *Synedra,* or extinct species having similar size and shape to *Fragilaria, Tabularia,* or *Synedra.* More generally, it is believed that such diatoms may be *Fragilariaceae,* or more generally *Fragilariales,* or more generally *Fragilariophyceae,* or more generally pennate diatoms, or extinct species having similar size and shape to *Fragilariaceae, Fragilariales, Fragilariophyceae,* or pennate diatoms. Herein, reference to "*Fragilaria*", "*Tabularia*", "*Synedra*", "*Fragilariaceae*", "*Fragilariales*", "*Fragilariophyceae*", or "pennate" diatoms in some embodiments may include, in addition to extant species known by such names, extinct species having similar size and shape to *Fragilaria, Tabularia, Synedra, Fragilariaceae, Fragilariales, Fragilariophyceae,* or pennate diatoms respectively.

Because the diatom frustules of CELATOM™ MN-51 appear to be more effective at killing bedbugs than other components of CELATOM™ MN-51 (see Experiment #9), because CELATOM™ MN-51 appears to be more effective in controlling bedbug populations than the other diatomaceous earth products described above (see Experiment #1, Experiment #2, and Experiment #6), and because CELATOM™ MN-51 appears to include one or more of remains of diatoms having frustules having widths less than about 3 micrometers or less than about 5 micrometers and lengths greater than about 20 micrometers or greater than about 30 micrometers, remains of *Fragilaria,* remains of *Tabularia,* remains of *Synedra,* remains of *Fragilariaceae,* remains of *Fragilariales,* remains of *Fragilariophyceae,* and remains of pennate diatoms, it is believed, without wishing to be bound by any theory, that one or more of remains of diatoms having frustules having widths less than about 3 micrometers or less than about 5 micrometers and lengths greater than about 20 micrometers or greater than about 30 micrometers, remains of *Fragilaria,* remains of *Tabularia,* remains of *Synedra,* remains of *Fragilariaceae,* remains of *Fragilariales,* remains of *Fragilariophyceae,* and remains of pennate diatoms may be more effective than other diatom remains at controlling bedbug populations. Again without wishing to be bound by any theory, it is believed that such diatom remains may be sharper than other diatom remains and thus more likely to pierce or otherwise damage exoskeletons such as bedbug exoskeletons.

Also without wishing to be bound by any theory, it is believed that the size and shape of some particles in CELATOM™ MN-51, such as one or more of remains of diatoms having frustules having widths less than about 3 micrometers or less than about 5 micrometers and lengths greater than about 20 micrometers or greater than about 30 micrometers, remains of *Fragilaria,* remains of *Tabularia,* remains of *Synedra,* remains of *Fragilariaceae,* remains of *Fragilariales,* remains of *Fragilariophyceae,* and remains of pennate diatoms, for example, may block or otherwise interfere with spiracles on exoskeletons of bedbugs, thereby diminishing or eliminating passage of air into the trachea of the bedbugs and potentially asphyxiating the bedbugs, more effectively than other types of diatomaceous earth.

Again without wishing to be bound by any theory, it is believed that in some embodiments, heat treatment or flash drying of CELATOM™ MN-51 may change the characteristics of the diatomaceous earth to be more abrasive and thus more damaging to animal exoskeletons, or more particularly to insect exoskeletons or to bedbug exoskeletons, and that such heat treatment or flash drying may also dry out the diatomaceous earth, thereby making the diatomaceous earth more absorbent to dehydrate and kill an animal or insect such as bedbug and potentially more effective in various embodiments including the various embodiments described herein.

Although CELATOM™ MN-51 has been discussed above, some embodiments may include alternative types of diatomaceous earth that may be supplied by other suppliers but that may include some characteristics of CELATOM™ MN-51 and that thus may have effectiveness similar to the effectiveness of CELATOM™ MN-51. In general, such alternative types of diatomaceous earth in some embodiments may also include one or more of: remains of diatoms having frustules having widths less than about 3 micrometers or less than about 5 micrometers and lengths greater than about 20 micrometers or greater than about 30 micrometers; remains of *Fragilaria*; remains of *Tabularia*; remains of *Synedra*; remains of *Fragilariaceae*; remains of *Fragilariales*; remains of *Fragilariophyceae*; and remains of pennate diatoms. Additionally or alternatively, such alternative types of diatomaceous earth in some embodiments may be heat-treated or flash dried diatomaceous earth, such as diatomaceous earth flash dried at about 480° C. for about 15 seconds for example, or may more generally be modified diatomaceous earth. Such alternative types of diatomaceous earth may also include other types of diatomaceous earth found in deposits formed from fresh-water diatoms, such as the deposit at Clark Station, Nev., United States of America for example. More generally, such alternative types of diatomaceous earth may have one or more properties similar to one or more of the properties of CELATOM™ MN-51 listed in Tables 1 and 2 above in order to achieve effects that may be similar to the effects of CELATOM™ MN-51 described above.

Because Experiment #9 appears to indicate that the smaller size fraction was significantly more effective than the larger size fraction at killing bedbugs, alternative embodiments may include a smaller size fraction of a size-separated diatomaceous earth instead of the diatomaceous earth itself. Again without wishing to be bound by any theory, it is believed that such smaller size fractions may include greater concentrations of relatively more effective diatom frustule remains. Additionally or alternatively, and again without wishing to be bound by any theory, it is believed that such smaller size fractions may more relatively effectively block or otherwise interfere with spiracles on exoskeletons of bedbugs, thereby diminishing or eliminating passage of air into the trachea of the bedbugs and potentially asphyxiating the bedbugs.

Therefore, in various embodiments, the size-separated diatomaceous earth may include CELATOM™ MN-51 for example, and may include diatomaceous earth size-separated by centrifuge. Further, in some embodiments, the smaller size fraction may include or consist of particles less than a separation size, such as about 11 micrometers for example. In embodiments where the diatomaceous earth is size separated by centrifuge, non-spherical particles may be size-separated such that the smaller size fraction may include elongate particles that are longer than the separation size. In general, size separating diatomaceous earth may prepare diatomaceous earth for use in controlling a population of insects, such as for use in the spray apparatus 100 shown in FIG. 1 for example.

Experiment #3, Experiment #4, and Experiment #5 appear to indicate that diatomaceous earth delivered from an aerosol product, such as the spray apparatus 100 shown in FIG. 1 for example, is effective at killing bedbugs, and thus in controlling bedbug populations, even if the bedbugs only contact the diatomaceous earth briefly when crossing an area sprayed with diatomaceous earth (see Experiment #4 and Experiment #5). In various embodiments, methods of using such an apparatus may include exposing bedbugs or other pests to diatomaceous earth, for example by spraying, propelling, or otherwise applying the diatomaceous earth to a surface. In some embodiments, when one bedbug contacts the diatomaceous earth, that bedbug may spread the diatomaceous earth to other bedbugs (see Experiment #6 and Experiment #7), and therefore causing one bedbug to contact diatomaceous earth may cause death of several bedbugs. Therefore, in some embodiments, spraying, propelling, or otherwise applying the diatomaceous earth to a surface where bedbugs are likely to be found may be effective even against bedbugs that do not contact the surface where the diatomaceous earth was applied.

Further, according to Experiment #8, quantities of dusts deposited on filter papers weighed less than diatomaceous earth residues deposited by spraying an aerosol formulation on filter papers. Again, without wishing to be bound by any theory, it is believed that perhaps diatomaceous earth delivered from an aerosol product has greater adhesiveness than a diatomaceous earth dust. The spray apparatus 100 and alternative embodiments may therefore apply diatomaceous earth to some surfaces (such as vertical or generally vertical surfaces of furniture for example) more durably for longer-lasting control of bedbug populations than when compared to other methods of applying diatomaceous earth to surfaces.

Also without wishing to be bound by any theory, it is believed that perhaps diatomaceous earth delivered from an aerosol product may be broken and reduced in size when compared to diatomaceous earth applied as a dust for example, perhaps from one or more of: crushing, such as from the ball bearing or marble 136 in response to shaking the body 102 in the embodiment shown in FIG. 1; shear stress in an aerosol can; turbulence in an aerosol can; and relatively high velocities from a propellant in an aerosol can.

Further, the spray apparatus 100 and alternative embodiments may be more convenient or effective in the control of such insect populations when compared to other methods of applying diatomaceous earth to surfaces. For example, the spray apparatus 100 and alternative embodiments may advantageously apply diatomaceous earth to a surface more evenly than when compared to other methods of applying diatomaceous earth to surfaces, because the propellant may cause a generally even spray of diatomaceous earth. In some embodiments, a more even application of diatomaceous earth may increase effectiveness of the diatomaceous earth by effectively covering a greater area of a surface, and may improve the appearance of the surface by avoiding more noticeable areas of high concentration of diatomaceous earth. Further, the spray apparatus 100 and alternative embodiments may enable a user to apply diatomaceous earth conveniently from a single apparatus, without having to transfer the diatomaceous earth from a container to a separate applicator apparatus as may be required in other methods of applying diatomaceous earth to surfaces.

In view of the foregoing, it is believed that some embodiments of the spray apparatus 100 and alternative embodiments may effectively control populations of insects such as bedbugs. Therefore, commercial use of embodiments of the spray apparatus 100 and of alternative embodiments may involve distributing, selling, offering for sale, placing, or otherwise using such spray apparatuses in an effort to control populations of animals, such as animals having exoskeletons, arthropods, arachnids, insects, and bedbugs for example.

PCT international patent application no. PCT/CA2012/000389 filed at the Canadian receiving office of the PCT on Apr. 26, 2012 describes and illustrates various furniture apparatuses such as a nightstand, a dresser, a bed, a mattress, and a headboard that may include one or more substantially thermoplastic bodies including diatomaceous earth, legume extracts, or both incorporated therein, and such furniture apparatuses according to some embodiments may assist in the control of bedbug and other insect populations. Therefore, commercial use of embodiments of the spray apparatus 100 and of alternative embodiments may also involve distributing, selling, offering for sale, placing, or otherwise using such spray apparatuses together with such furniture apparatuses in an effort to control populations of animals, such as animals having exoskeletons, arthropods, arachnids, insects, and bedbugs for example.

As indicated in PCT international patent application no. PCT/CA2012/000389 filed at the Canadian receiving office of the PCT on Apr. 26, 2012, in some embodiments of furniture apparatuses, one or more internal surfaces may be darkly coloured, such as coloured black or another dark colour. Thus, for example when diatomaceous earth is applied to such internal surfaces with an embodiment of the spray apparatus 100 or an alternative embodiment, the lighter colour of the diatomaceous earth may make the diatomaceous earth more easily visible on such surfaces, and may facilitate noticing an absence of such products on such surfaces. Therefore, such darkly coloured internal surfaces in some embodiments may assist with visibly determining whether such internal surfaces have been sprayed or otherwise treated with diatomaceous earth or another more lightly coloured product, and such visual determinations may facilitate determining where and when such diatomaceous earth or other products should be applied to ensure a desired amount of such diatomaceous earth or other products on various furniture apparatuses. More generally, an embodiment of the spray apparatus 100 shown in FIG. 1 or an alternative embodiment may facilitate applying diatomaceous earth to surfaces where bedbugs may be introduced into a room, such as a bed, dresser, or side table where bedbugs may be introduced by occupants or from belongs of occupants of a room, or other surfaces where bedbugs may be likely to travel.

Diatomaceous earth is a natural product, and in some embodiments, natural products may be preferable over other pest control products, such as synthetic pesticides for example, because natural products may be less harmful to humans, to other life, or more generally to the environment. In view of the foregoing, the spray apparatus 100 shown in FIG. 1 and alternative embodiments may be advantageous when compared to other methods of controlling bedbug and other insect populations.

Although specific embodiments have been described and illustrated, such embodiments should be considered illustrative only and not as limiting the invention as construed in accordance with the accompanying claims.

What is claimed is:

1. A spray apparatus comprising:
    a body defining a reservoir holding contents comprising diatomaceous earth and a compressed propellant for propelling the diatomaceous earth from the reservoir, wherein the diatomaceous earth comprises remains of pennate diatoms; and
    an actuator for controllably releasing the propellant and the diatomaceous earth propelled by the propellant from the reservoir.

2. The apparatus of claim 1 wherein the pennate diatoms comprise *Fragilariophyceae* diatoms.

3. The apparatus of claim 2 wherein the *Fragilariophyceae* diatoms comprise *Fragilariales* diatoms.

4. The apparatus of claim 3 wherein the *Fragilariales* diatoms comprise *Fragilariaceae* diatoms.

5. The apparatus of claim 4 wherein the *Fragilariaceae* diatoms comprise diatoms selected from the group consisting of *Synedra* diatoms, *Tabularia* diatoms, and *Fragilaria* diatoms.

6. The apparatus of claim 1 wherein the diatomaceous earth comprises remains of diatoms having frustules having widths less than about 5 micrometers and lengths greater than about 20 micrometers.

7. The apparatus of claim 1 wherein the diatomaceous earth comprises remains of diatoms having frustules having widths less than about 3 micrometers and lengths greater than about 20 micrometers.

8. The apparatus of claim 1 wherein the diatomaceous earth comprises remains of diatoms having frustules having widths less than about 5 micrometers and lengths greater than about 30 micrometers.

9. The apparatus of claim 1 wherein the diatomaceous earth comprises remains of diatoms having frustules having widths less than about 3 micrometers and lengths greater than about 30 micrometers.

10. The apparatus of claim 1 wherein the diatomaceous earth comprises a smaller size fraction of particles less than about 11 micrometers in size.

11. The apparatus of claim 1 wherein the diatomaceous earth is flash dried.

12. The apparatus of claim 1 wherein the diatomaceous earth comprises diatomaceous earth from Clark Station, Nevada, United States of America.

13. The apparatus of claim 1 wherein the diatomaceous earth is at least about 3% by weight of the contents.

14. The apparatus of claim 1 wherein the diatomaceous earth is at least about 5% by weight of the contents.

15. The apparatus of claim 1 wherein the diatomaceous earth is at least about 7% by weight of the contents.

16. The apparatus of claim 5 wherein the diatomaceous earth is about 8% by weight of the contents.

17. A method of pest control, the method comprising exposing pests to diatomaceous earth comprising remains of pennate diatoms.

18. The method of claim 17 wherein the pennate diatoms comprise pennate diatoms selected from the group consisting of *Fragilariophyceae* diatoms, *Fragilariales* diatoms, *Fragilariaceae* diatoms, *Synedra* diatoms, *Tabularia* diatoms, and *Fragilaria* diatoms.

19. The method of claim 17 wherein the diatomaceous earth comprises remains of diatoms having frustules having widths less than about 5 micrometers and lengths greater than about 20 micrometers.

20. The method of claim 17 wherein the diatomaceous earth comprises a smaller size fraction of particles less than about 11 micrometers in size.

21. The method of claim 17 wherein exposing the pests to the diatomaceous earth comprises causing a compressed propellant to propel the diatomaceous earth on a surface.

22. A method of preparing diatomaceous earth for use as a pesticide, the method comprising size separating the diatomaceous earth into a smaller size fraction and into a larger size fraction.

23. The method of claim 22 wherein the smaller size fraction is a smaller size fraction of particles less than about 11 micrometers in size.

24. The method of claim 17 wherein the pests comprise insects.

25. The method of claim 24 wherein the insects comprise bedbugs.

26. The method of claim 17 wherein the pests comprise arachnids.

27. A furniture apparatus comprising a surface and comprising diatomaceous earth applied to the surface, wherein the diatomaceous earth comprises remains of pennate diatoms.

28. The apparatus of claim 27 wherein the pennate diatoms comprise pennate diatoms selected from the group consisting of *Fragilariophyceae* diatoms, *Fragilariales* diatoms, *Fragilariaceae* diatoms, *Synedra* diatoms, *Tabularia* diatoms, and *Fragilaria* diatoms.

29. The apparatus of claim 27 wherein the diatomaceous earth comprises a smaller size fraction of particles less than about 11 micrometers in size.

30. The apparatus of claim 27 wherein the apparatus is selected from the group consisting of a nightstand, a dresser, a bed, a mattress, and a headboard.

* * * * *